(12) United States Patent
Namai et al.

(10) Patent No.: US 9,323,146 B2
(45) Date of Patent: Apr. 26, 2016

(54) PHOTORESIST COMPOSITION, RESIST PATTERN-FORMING METHOD, COMPOUND, ACID GENERATING AGENT, AND PHOTODEGRADABLE BASE

(71) Applicant: JSR CORPORATION, Minato-ku (JP)

(72) Inventors: Hayato Namai, Tokyo (JP); Kazuo Nakahara, Tokyo (JP); Norihiko Ikeda, Tokyo (JP)

(73) Assignee: JSR CORPORATION, Minato-ku (JP)

( * ) Notice: Subject to any disclaimer, the term of this patent is extended or adjusted under 35 U.S.C. 154(b) by 0 days.

(21) Appl. No.: 14/470,108

(22) Filed: Aug. 27, 2014

(65) Prior Publication Data

US 2014/0363769 A1    Dec. 11, 2014

Related U.S. Application Data

(63) Continuation of application No. PCT/JP2013/054618, filed on Feb. 22, 2013.

(30) Foreign Application Priority Data

Feb. 27, 2012 (JP) ................. 2012-040802

(51) Int. Cl.
| | | |
|---|---|---|
| G03F 7/004 | (2006.01) | |
| C07D 317/70 | (2006.01) | |
| G03F 7/039 | (2006.01) | |
| G03F 7/11 | (2006.01) | |
| G03F 7/20 | (2006.01) | |

(52) U.S. Cl.
CPC ............ *G03F 7/0045* (2013.01); *C07D 317/70* (2013.01); *G03F 7/0046* (2013.01); *G03F 7/0397* (2013.01); *G03F 7/11* (2013.01); *G03F 7/20* (2013.01); *G03F 7/2041* (2013.01)

(58) Field of Classification Search
None
See application file for complete search history.

(56) References Cited

U.S. PATENT DOCUMENTS

2011/0014568 A1    1/2011   Ichikawa et al.

FOREIGN PATENT DOCUMENTS

| JP | 2004-210670 A | 7/2004 |
|---|---|---|
| JP | 2004-307387 A | 11/2004 |
| JP | 2007-145797 A | 6/2007 |
| JP | 2010-250063 A | 11/2010 |
| JP | 2011-37837 A | 2/2011 |
| JP | 2012-193160 A | 10/2012 |
| JP | 2013-33161 A | 2/2013 |
| WO | WO 2013047091 A1 * | 4/2013 |

OTHER PUBLICATIONS

Machine translation JP 2010-250063. Nov. 4, 2010.*
Machine translation JP 2004-210670. Jul. 29, 2004.*
International Search Report issued Mar. 19, 2013 in PCT/JP2013/054618.

* cited by examiner

*Primary Examiner* — Cynthia H Kelly
*Assistant Examiner* — Alyssa L Cepluch
(74) *Attorney, Agent, or Firm* — Oblon, McClelland, Maier & Neustadt, L.L.P.

(57) ABSTRACT

A photoresist composition containing a polymer having a structural unit including an acid-labile group, and a compound represented by the formula (1). In the formula (1), $R^1$ represents a hydrogen atom or a monovalent acid-labile group. $R^2$ represents an alicyclic hydrocarbon group having 3 to 20 carbon atoms and a valency of (m+1). m is an integer of 2 to 5. $R^3$ and $R^4$ each independently represent a hydrogen atom, a fluorine atom, a monovalent hydrocarbon group having 1 to 20 carbon atoms or a monovalent fluorinated hydrocarbon group having 1 to 20 carbon atoms. n is an integer of 0 to 5. At least two of a plurality of $R^1$s optionally taken together represent a ring structure, together with a plurality of oxygen atoms bonding to $R^1$ and the carbon atom(s) constituting $R^2$ and bonding to these oxygen atoms. $M^+$ represents a monovalent radiation-degradable onium cation.

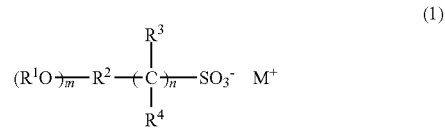

(1)

18 Claims, No Drawings

PHOTORESIST COMPOSITION, RESIST PATTERN-FORMING METHOD, COMPOUND, ACID GENERATING AGENT, AND PHOTODEGRADABLE BASE

TECHNICAL FIELD

The present invention relates to a photoresist composition, a resist pattern-forming method, a compound, an acid generating agent and a photodegradable base.

BACKGROUND ART

Chemically amplified photoresist compositions generate an acid upon irradiation with e.g., a far ultraviolet ray typified by a KrF excimer laser beam (wavelength: 248 nm), an ArF excimer laser beam (wavelength: 193 nm) and the like, or an electron beam at a light-exposed site, and chemical reactions catalyzed by the acid cause a difference of the rate of dissolution of the light-exposed site and a light-unexposed site in a developer solution, thereby enabling a resist pattern to be formed on a substrate.

For the photoresist compositions, superior resolving ability and a superior pattern configuration have been demanded with the advance of microfabrication technologies. To address the demand, a variety of acid generating agents to be incorporated into a photoresist composition have been investigated; for example, a sulfonic acid salt having a bulky group, and the like have been developed (see Japanese Unexamined Patent Application, Publication Nos. 2004-307387 and 2007-145797).

However, in these days when further miniaturization of resist pattern is advancing, levels of performances expected for resist patterns are further elevated, and conventional photoresist compositions fail to sufficiently satisfy the resolving ability, an LWR (Line Width Roughness) performance, which is an indicative of a variation in the line width, and the like.

PRIOR ART DOCUMENTS

Patent Documents

Patent Document 1: Japanese Unexamined Patent Application, Publication No. 2004-307387
Patent Document 2: Japanese Unexamined Patent Application, Publication No. 2007-145797

SUMMARY OF THE INVENTION

Problems to be Solved by the Invention

The present invention was made in view of the foregoing circumstances, and an object of the invention is to provide: a photoresist composition and a resist pattern-forming method enabling superior resolving ability and a superior LWR performance to be exhibited; a novel compound suitable for an improvement of the resolving ability and LWR performance of the photoresist composition; as well as an acid generating agent and a photodegradable base that contain the compound.

Means for Solving the Problems

According to an aspect of the invention made for solving the aforementioned problems, a photoresist composition is provided that contains:

a polymer having a structural unit that includes an acid-labile group (hereinafter, may be also referred to as "(A) polymer" or "polymer (A)"); and a compound represented by the following formula (1) (hereinafter, may be also referred to as "(B) compound" or "compound (B)").

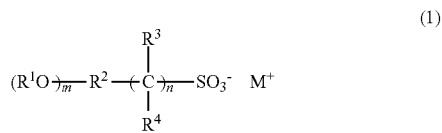

In the formula (1), $R^1$ represents a hydrogen atom or a monovalent acid-labile group; $R^2$ represents an alicyclic hydrocarbon group having 3 to 20 carbon atoms and a valency of (m+1); m is an integer of 2 to 5; $R^3$ and $R^4$ each independently represent a hydrogen atom, a fluorine atom, a monovalent hydrocarbon group having 1 to 20 carbon atoms or a monovalent fluorinated hydrocarbon group having 1 to 20 carbon atoms; n is an integer of 0 to 5, wherein a plurality of $R^1$s are identical to or different from each other, a plurality of $R^3$s, in a case where $R^3$ is present in a plurality of number, are identical to or different from each other, and a plurality of $R^4$s, in a case where $R^4$ is present in a plurality of number, are identical to or different from each other, and wherein at least two of the plurality of $R^1$s optionally taken together represent a ring structure by binding with each other, together with a plurality of oxygen atoms that bond to $R^1$ and the carbon atom or carbon atoms constituting $R^2$ and bonding to these oxygen atoms; and $M^+$ represents a monovalent radiation-degradable onium cation.

When the photoresist composition contains the compound (B) that contains a hydroxy group or a group generating a hydroxy group by an action of an acid, the resolving ability and LWR performance thereof can be improved. Although it is not necessarily clear why the photoresist composition exhibits the aforementioned effect when the photoresist composition contains the compound (B) that has the aforementioned structure, it may be presumed, for example, that since the compound (B) includes a hydroxy group after an exposure, the interaction with a polymer component constituting the photoresist composition may be enhanced, leading to a proper reduction of a diffusion length of the acid generated from the compound (B), or the like.

It is preferred that $M^+$ in the above formula (1) is represented by the following formula (2).

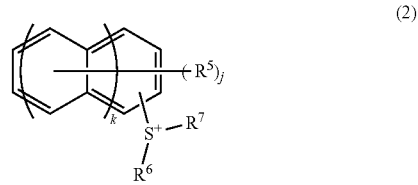

In the formula (2), $R^5$ represents a fluorine atom, a hydroxy group, an alkyl group having 1 to 10 carbon atoms, an alkoxy group having 1 to 10 carbon atoms, an alkoxycarbonyl group having 2 to 11 carbon atoms, or an alkylsulfonyl group having 1 to 10 carbon atoms; j is an integer of 0 to 9, wherein in a case where j is no less than 2, a plurality of $R^5$s are identical or different; $R^6$ and $R^7$ each independently represent an alkyl group having 1 to 10 carbon atoms or an aryl group having 6 to 20 carbon atoms, wherein a part or all of hydrogen atoms included in the alkyl group and the aryl group are unsubstituted or substituted, and wherein $R^6$ and $R^7$ optionally taken together represent a ring structure having 2 to 10 carbon atoms by binding with each other, together with the sulfur atom to which $R^6$ and $R^7$ bond; and k is an integer of 0 to 2.

When $M^+$ in the above formula (1) is thus the radiation-degradable onium cation represented by the above formula (2), the resolving ability and LWR performance of the photoresist composition may be further improved.

It is preferred that $R^2$ in the above formula (1) represents a polycyclic alicyclic hydrocarbon group. It is presumed that when $R^2$ thus represents the specific group, an acid generated from the compound (B) has more bulkiness, leading to a more proper diffusion length of the acid. As a result, the photoresist composition that contains the compound (B) may exhibit more superior resolving ability and a more superior LWR performance.

It is preferred that $(R^1O)_m$— in the above formula (1) is represented by the following formula (Y).

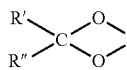
(Y)

In the formula (Y), R' and R" each independently represent a hydrocarbon group having 1 to 10 carbon atoms, wherein R' and R" optionally taken together represent a ring structure by binding with each other, together with the carbon atom to which R' and R" bond.

When $(R^1O)_m$— in the above formula (1) thus represents the specific structure, the resolving ability and LWR performance of the photoresist composition can be further improved.

In a case where n is an integer of 1 to 5, among $R^3(s)$ and $R^4(s)$ in the above formula (1), $R^3$ and $R^4$ that bond to the carbon atom adjacent to the $SO_3^-$ group preferably represent a fluorine atom or a perfluoroalkyl group. When the compound (B) is contained, and the acid generating agent in which in the above formula (1), n is an integer of 1 to 5, and $R^3$ and $R^4$ that bond to the carbon atom adjacent to the $SO_3^-$ group among $R^3(s)$ and $R^4(s)$ represent a fluorine atom or a perfluoroalkyl group is contained, the resolving ability and LWR performance of the photoresist composition may be improved. This may be because when the acid generating agent contained in the photoresist composition contains the compound (B) that has the specific structure, the acid includes a hydroxy group after the exposure and the acidity of the generated acid may be properly enhanced.

It is preferred that the compound represented by the above formula (1) is represented by the following formula (1-I):

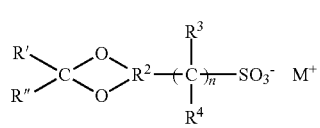
(1-I)

wherein, in the formula (1-I), $R^2$ represents a trivalent alicyclic hydrocarbon group having 3 to 20 carbon atoms; $R^3$ and $R^4$ each independently represent a hydrogen atom, a fluorine atom, a monovalent hydrocarbon group having 1 to 20 carbon atoms or a monovalent fluorinated hydrocarbon group having 1 to 20 carbon atoms; R' and R" each independently represent a hydrocarbon group having 1 to 10 carbon atoms, wherein R' and R" optionally taken together represent a ring structure by binding with each other, together with the carbon atom to which R' and R" bond; n is an integer of 0 to 5, wherein in a case where $R^3$ and $R^4$ are each present in a plurality of number, a plurality of $R^3$s are identical to or different from each other, and a plurality of $R^4$s are identical to or different from each other; and $M^+$ represents a monovalent radiation-degradable onium cation.

It is more preferred that the compound represented by the above formula (1) is represented by the following formula (1-i):

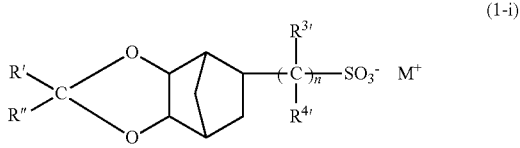
(1-i)

wherein, in the formula (1-i), n is an integer of 0 to 5; R' and R" each independently represent a hydrocarbon group having 1 to 10 carbon atoms, wherein R' and R" optionally taken together represent a ring structure by binding with each other, together with the carbon atom to which R' and R" bond; $R^{3'}$ and $R^{4'}$ each independently represent a fluorine atom or a perfluoroalkyl group, wherein in a case where $R^{3'}$ and $R^{4'}$ are each present in a plurality of number, a plurality of $R^{3'}$'s are identical to or different from each other, and a plurality of $R^{4'}$'s are identical to or different from each other; and $M^+$ represents a monovalent radiation-degradable onium cation.

When the compound represented by the above formula (1) has thus the specific structure, the resolving ability and LWR performance of the photoresist composition may be further improved.

In a case where n is an integer of 1 to 5, $R^3$ and $R^4$ that bond to the carbon atom adjacent to the $SO_3^-$ group among $R^3(s)$ and $R^4(s)$ in the above formula (1) preferably represent a hydrogen atom or an alkyl group having 1 to 10 carbon atoms. When the compound (B) is contained, and the photodegradable base in which in the above formula (1), n is an integer of 1 to 5, and $R^3$ and $R^4$ that bond to the carbon atom adjacent to the $SO_3^-$ group among $R^3(s)$ and $R^4(s)$ represent a hydrogen atom or an alkyl group having 1 to 10 carbon atoms is contained, the resolving ability and LWR performance of the photoresist composition may be improved. This may be because when the photodegradable base contained in the photoresist composition contains the compound having the specific structure, a diffusing acid can be trapped at a light-unexposed site, whereas the function of trapping the acid is lost at a light-exposed site.

It is preferred that the polymer (A) further has a structural unit that includes a hydroxy group. When the polymer (A) further has a structural unit that includes a hydroxy group, the interaction with the acid generated from the compound (B) may be further enhanced, and a more proper diffusion length of the acid generated from the compound (B) may be attained. As a result, the resolving ability and LWR performance of the photoresist composition can be further improved.

According to another aspect of the present invention, a resist pattern-forming method includes:
providing a resist film on a substrate using the photoresist composition according to the aspect of the present invention;
exposing the resist film; and
developing the resist film exposed.

According to the resist pattern-forming method, since the photoresist composition according to the aspect of the present invention is used, a resist pattern exhibiting a superior resolution and a decreased LWR can be formed.

According to still another aspect of the present invention, a compound represented by the following formula (1) (hereinafter, may be also referred to as "compound (1)") is provided.

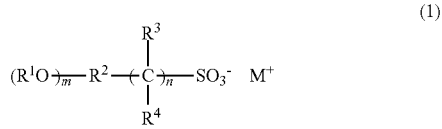
(1)

In the formula (1), $R^1$ represents a hydrogen atom or a monovalent acid-labile group; $R^2$ represents an alicyclic hydrocarbon group having 3 to 20 carbon atoms and a valency of (m+1); m is an integer of 2 to 5; $R^3$ and $R^4$ each independently represent a hydrogen atom, a fluorine atom, a monovalent hydrocarbon group having 1 to 20 carbon atoms or a monovalent fluorinated hydrocarbon group having 1 to 20 carbon atoms; n is an integer of 0 to 5, wherein a plurality of $R^1$s are identical to or different from each other, a plurality of $R^3$s, in a case where $R^3$ is present in a plurality of number, are identical to or different from each other, and a plurality of $R^4$s, in a case where $R^4$ is present in a plurality of number, are identical to or different from each other, and wherein at least two of the plurality of $R^1$s optionally taken together represent a ring structure by binding with each other, together with a plurality of oxygen atoms that bond to R' and the carbon atom or carbon atoms constituting $R^2$ and bonding to these oxygen atoms; and $M^+$ represents a monovalent radiation-degradable onium cation.

When the compound (1) according to the aspect of the present invention includes a hydroxy group or a group generating a hydroxy group by an action of an acid, the resolving ability and LWR performance of the photoresist composition containing the compound (1) can be improved. Although it is not necessarily clear why the compound (1) exhibits the aforementioned effect when the compound (1) has the aforementioned structure, it is presumed, for example, that since the compound (1) includes a hydroxy group after an exposure, the interaction with a polymer component constituting the photoresist composition may be enhanced, leading to a proper reduction of the diffusion length of the acid generated from the compound (1), or the like.

It is preferred that $M^+$ in the above formula (1) is represented by the following formula (2).

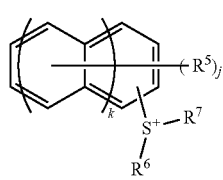
(2)

In the formula (2), $R^5$ represents a fluorine atom, a hydroxy group, an alkyl group having 1 to 10 carbon atoms, an alkoxy group having 1 to 10 carbon atoms, an alkoxycarbonyl group having 2 to 11 carbon atoms, or an alkylsulfonyl group having 1 to 10 carbon atoms; j is an integer of 0 to 9, wherein in a case where j is no less than 2, a plurality of $R^5$s are identical or different; $R^6$ and $R^7$ each independently represent an alkyl group having 1 to 10 carbon atoms or an aryl group having 6 to 20 carbon atoms, wherein a part or all of hydrogen atoms included in the alkyl group and the aryl group are unsubstituted or substituted, and wherein $R^6$ and $R^7$ optionally taken together represent a ring structure having 2 to 10 carbon atoms by binding with each other, together with the sulfur atom to which $R^6$ and $R^7$ bond; and k is an integer of 0 to 2.

When $M^+$ in the above formula (1) thus represents the radiation-degradable onium cation represented by the above formula (2), the resolving ability and LWR performance of the photoresist composition may be further enhanced.

It is preferred that $R^2$ in the above formula (1) represents a polycyclic alicyclic hydrocarbon group. It is presumed that when $R^2$ thus represents the specific group, the acid generated from the compound (1) has more bulkiness, leading to a more proper diffusion length of the acid. As a result, more superior resolving ability and a more superior LWR performance of the photoresist composition that contains the compound may be attained.

It is preferred that $(R^1O)_m$— in the above formula (1) is represented by the following formula (Y).

(Y)

In the formula (Y), R' and R" each independently represent a hydrocarbon group having 1 to 10 carbon atoms, wherein R' and R" optionally taken together represent a ring structure by binding with each other, together with the carbon atom to which R' and R" bond.

When $(R^1O)_m$— in the above formula (1) thus represents the specific structure, the resolving ability and LWR performance of the photoresist composition can be further improved.

According to yet still another aspect of the present invention, a compound represented by the following formula (1-I) is provided,

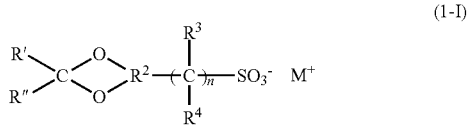
(1-I)

wherein, in the formula (1-I), $R^3$, $R^4$, n and $M^+$ are as defined in the above formula (1); $R^2$ represents a trivalent alicyclic hydrocarbon group having 3 to 20 carbon atoms; R' and R" each independently represent a hydrocarbon group having 1 to 10 carbon atoms, wherein R' and R" optionally taken together represent a ring structure by binding with each other, together with the carbon atom to which R' and R" bond, and wherein in a case where $R^3$ and $R^4$ are each present in a plurality of number, a plurality of $R^3$s are identical to or different from each other, and a plurality of $R^4$s are identical to or different from each other.

According to yet still another aspect of the present invention, a compound represented by the following formula (1-i) is provided,

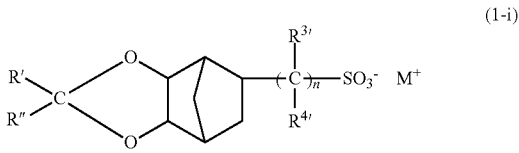

(1-i)

wherein, in the formula (1-i), n and $M^+$ are as defined in the above formula (1); R' and R" each independently represent a hydrocarbon group having 1 to 10 carbon atoms, wherein R' and R" optionally taken together represent a ring structure by binding with each other, together with the carbon atom to which R' and R" bond; and $R^{3'}$ and $R^{4'}$ each independently represent a fluorine atom or a perfluoroalkyl group, wherein in a case where $R^{3'}$ and $R^{4'}$ are each present in a plurality of number, a plurality of $R^{3'}$'s are identical to or different from each other, and a plurality of $R^{4'}$'s are identical to or different from each other.

When the compound represented by the above formula (1-i) has the specific structure, the resolving ability and LWR performance of a photoresist composition that contains the compound may be improved.

According to yet still another aspect of the present invention, an acid generating agent contains the compound according to the still another aspect of the present invention, wherein n is an integer of 1 to 5; and among $R^3$(s) and $R^4$(s) in the above formula (1), $R^3$ and $R^4$ that bond to the carbon atom adjacent to the $SO_3^-$ group represent a fluorine atom or a perfluoroalkyl group. When the acid generating agent contains the compound having the specific structure, the acid includes a hydroxy group after the exposure and the acidity of the generated acid may be properly enhanced. As a result, the resolving ability and LWR performance of the photoresist composition that contains the acid generating agent according to yet still another aspect of the present invention can be improved.

According to even yet still another aspect of the present invention, a photodegradable base contains the compound according to the still another aspect of the present invention, wherein n is an integer of 1 to 5; and among $R^3$(s) and $R^4$(s) in the above formula (1), $R^3$ and $R^4$ that bond to the carbon atom adjacent to the $SO_3^-$ group represent a hydrogen atom or an alkyl group having 1 to 10 carbon atoms. When the photodegradable base contains the compound having the specific structure, a diffusing acid can be trapped at a light-unexposed site, whereas the function of trapping the acid is lost at a light-exposed site. As a result, the resolving ability and LWR performance of the photoresist composition that contains the photodegradable base can be improved.

"Organic group" as referred to herein means a group having at least one carbon atom.

Effects of the Invention

The photoresist composition, the resist pattern-forming method, the compound, the acid generating agent and the photodegradable base according to the aspects of the present invention enable a resist pattern exhibiting a superior resolution and a decreased LWR to be formed. Therefore, the photoresist composition, the compound, the acid generating agent and the photodegradable base can be suitably used in lithography processes for which further miniaturization is desired.

DESCRIPTION OF EMBODIMENTS

Photoresist Composition

A photoresist composition according to an embodiment of the present invention contains (A) a polymer having a structural unit that includes an acid-labile group, and (B) a compound. In addition, the photoresist composition may contain, as a favorable component, (C) a fluorine atom-containing polymer, (D) an acid diffusion controller or (E) a solvent, as described later. Moreover, other optional component(s) may be contained within a range not leading to impairment of the effects of the present invention. Hereinafter, each component will be explained in detail.

(A) Polymer

A specific structure of the polymer (A) is not particularly limited as long as the polymer (A) has a structural unit that includes an acid-labile group (hereinafter, may be also referred to as "structural unit (I)"). In addition, the polymer (A) preferably has, as a structural unit other than the structural unit (I), a structural unit (II) that includes at least one type of structure selected from the group consisting of a lactone structure, a cyclic carbonate structure and a sultone structure, and a structural unit that includes a hydroxy group (hereinafter, may be also referred to as "structural unit (III)"). Furthermore, the polymer (A) may have other structural unit within a range not leading to impairment of the effects of the present invention, and the polymer (A) may have two or more types of each structural unit. Hereinafter, each structural unit will be explained in detail.

Structural Unit (I)

The structural unit (I) includes an acid-labile group. According to the photoresist composition, at a light-exposed site, the acid-labile group in the structural unit (I) is dissociated by an action of an acid generated from the compound (B), whereby the solubility of the polymer (A) in a developer solution is altered, leading to the formation of a resist pattern. The "acid-labile group" in the structural unit (I) means a group that substitutes a hydrogen atom of a polar group such as e.g., a carboxy group and a hydroxy group, and is dissociated in the presence of an acid. Although the structural unit (I) is not particularly limited as long as the structural unit (I) includes an acid-labile group, examples thereof include a structural unit represented by the following formula (3).

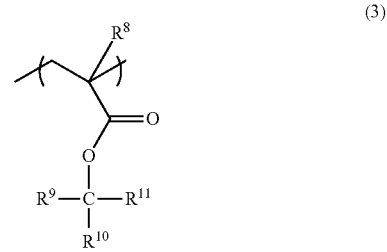

(3)

In the formula (3), $R^8$ represents a hydrogen atom, a fluorine atom, a methyl group or a trifluoromethyl group; and $R^9$ to $R^{11}$ each independently represent an alkyl group having 1 to 6 carbon atoms or an alicyclic hydrocarbon group having 4 to 20 carbon atoms, wherein $R^9$ and $R^{10}$ optionally taken together represent a divalent alicyclic hydrocarbon group by binding with each other, together with the carbon atom to which $R^9$ and $R^{10}$ bond.

Examples of the alkyl group having 1 to 6 carbon atoms which may be represented by $R^9$ to $R^{11}$ include a methyl group, an ethyl group, a propyl group, and the like.

Examples of the alicyclic hydrocarbon group having 4 to 20 carbon atoms which may be represented by $R^9$ to $R^{11}$ include a cyclobutyl group, a cyclopentyl group, a cyclohexyl group, a cyclooctyl group, an adamantyl group, and the like.

Examples of the divalent alicyclic hydrocarbon group optionally taken together represented by $R^9$ and $R^{10}$ by binding with each other include a cyclopentanediyl group, a norbornanediyl group, an adamantanediyl group, and the like.

The structural unit (I) is exemplified by structural units represented by the following formulae (3-1) to (3-12).

(3-1)
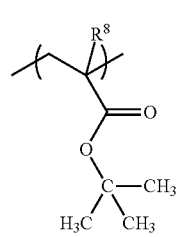

(3-2)
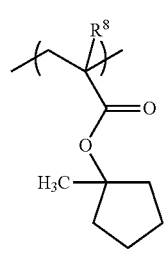

(3-3)
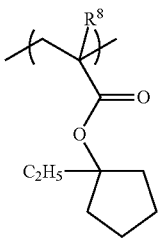

(3-4)
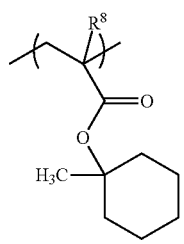

(3-5)
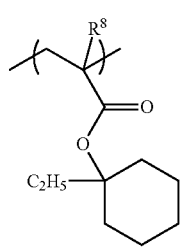

(3-6)
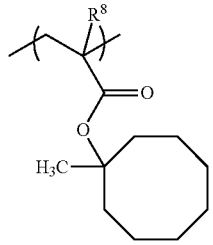

(3-7)
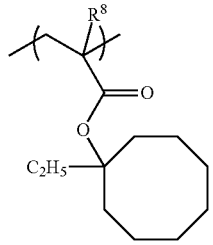

(3-8)
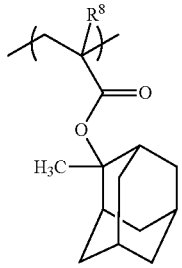

(3-9)
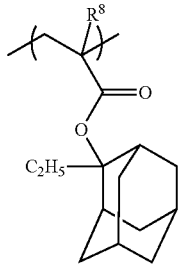

(3-10)
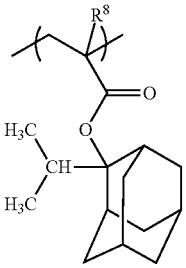

(3-11)
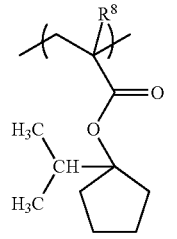

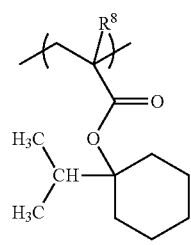
(3-12)

In the above formula, $R^8$ is as defined in the above formula (3).

Among the structural units, the structural units represented by the above formulae (3-2), (3-3) and (3-9) are preferred.

The proportion of the structural unit (I) in the polymer (A) with respect to the total structural units constituting the polymer (A) is preferably no less than 5 mol % and no greater than 90 mol %, and more preferably no less than 10 mol % and no greater than 85 mol %. When the proportion of the structural unit (I) in the polymer (A) falls within the abovementioned range, the sensitivity, etc. of the photoresist composition may be further improved.

Structural Unit (II)

The polymer (A) preferably has a structural unit (II) that includes at least one type of structure selected from the group consisting of a lactone structure, a cyclic carbonate structure and a sultone structure. When the polymer (A) has the structural unit (II), the adhesiveness of the resist film to a substrate, etc. can be increased.

The structural unit (II) is exemplified by structural units represented by the following formulae.

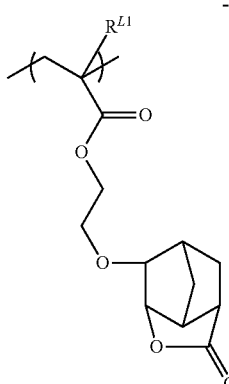 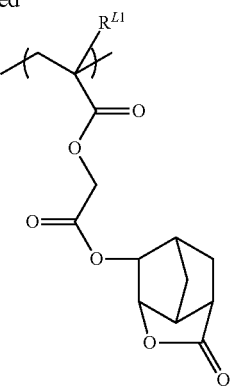

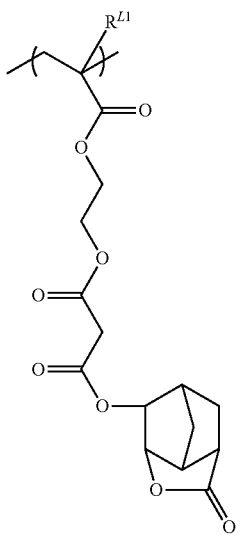 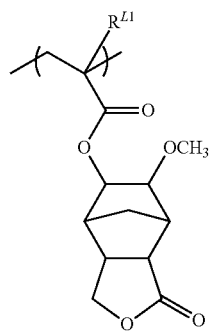

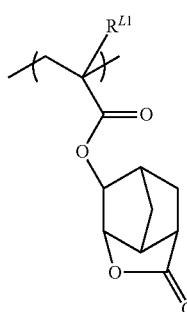 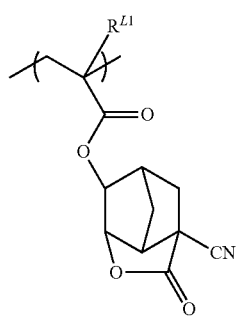 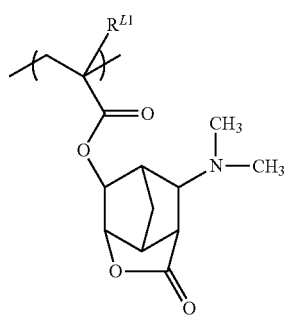 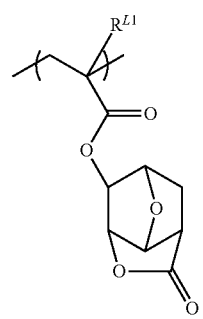

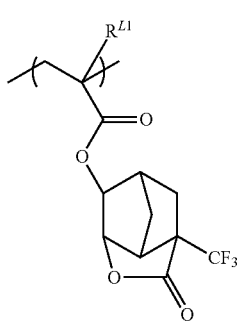 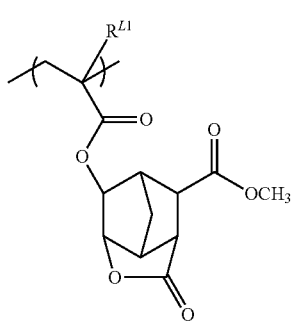 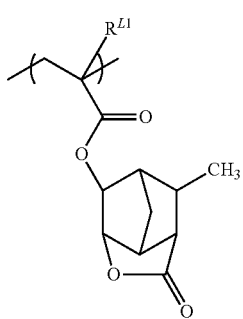 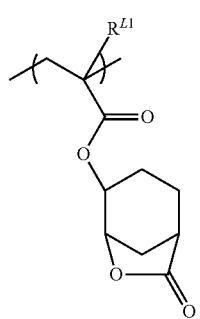

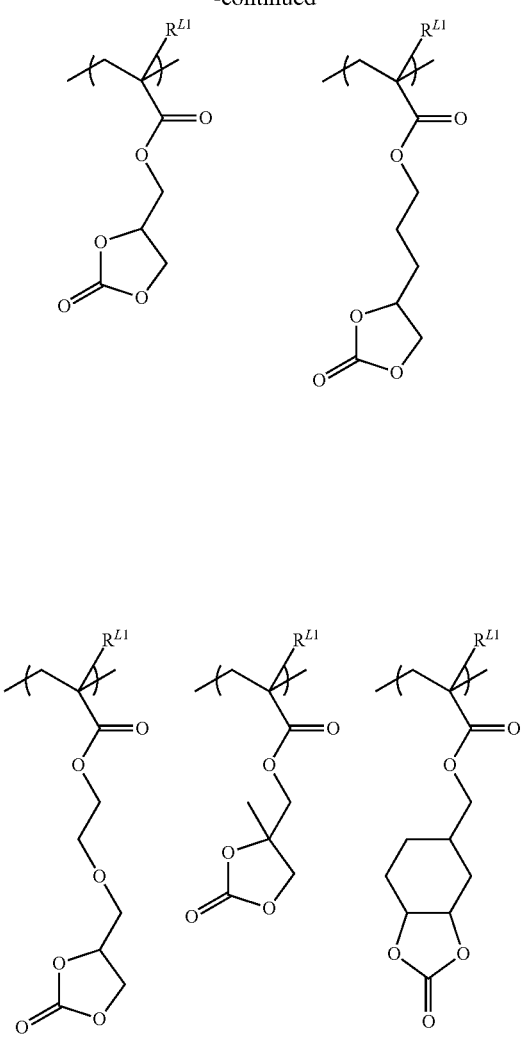
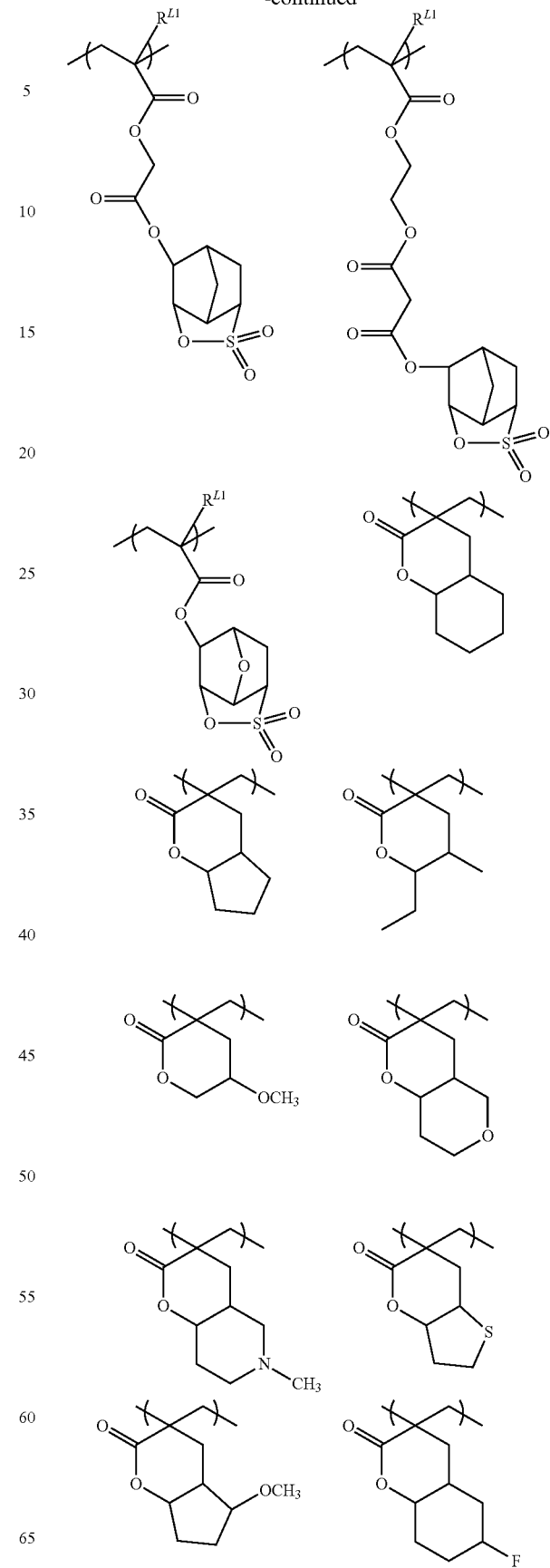

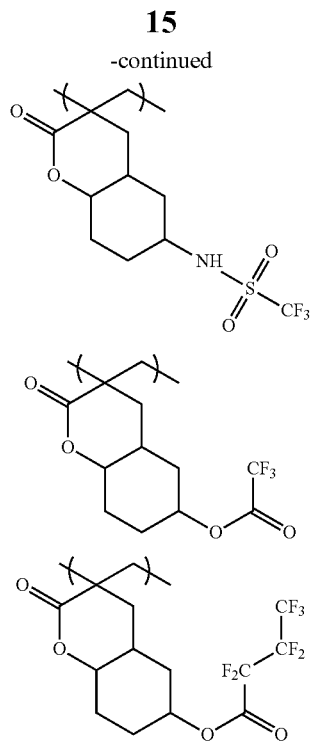

In the above formulae, $R^{L1}$ represents a hydrogen atom, a fluorine atom, a methyl group or a trifluoromethyl group.

Among the structural units, structural units derived from (meth)acrylic acid norbornanelactonyl esters are preferred.

The proportion of the structural unit (II) in the polymer (A) with respect to the total structural units constituting the polymer (A) is preferably no less than 0 mol % and no greater than 65 mol %, and more preferably no less than 15 mol % and no greater than 60 mol %. When the proportion of the structural unit (II) falls within the abovementioned range, the adhesiveness of the resist film to a substrate may be further increased.

Structural Unit (III)

The structural unit (III) includes a hydroxy group. When the polymer (A) further has the structural unit (III) in addition to the structural unit (I), the interaction with an acid generated from the compound (B) may be further enhanced, leading to a more proper diffusion length of the acid generated from the compound. As a result, the resolving ability and LWR performance of the photoresist composition can be further improved.

Although the structural unit (III) is not particularly limited as long as a hydroxy group is included, examples thereof include structural units represented by the following formulae (III-1) to (III-4) (hereinafter, may be also referred to as "structural units (III-1) to (III-4)"), and the like.

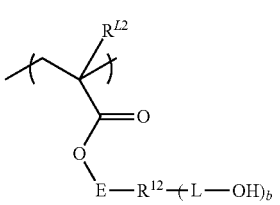

(III-1)

(III-2)

(III-3)

(iii)

(III-4)

In the above formulae (III-1) and (III-2), $R^{L2}$ represents a hydrogen atom, a fluorine atom, a methyl group or a trifluoromethyl group.

In the above formula (III-1), E represents a divalent acid-labile group; $R^{12}$ represents an alicyclic hydrocarbon group having a valency of (b+1); and b is an integer of 1 to 3.

In the above formulae (III-1) and (iii), L represents a divalent hydrocarbon group, wherein in a case where L is present in a plurality of number, a plurality of Ls are identical or different.

In the above formula (III-2), $R^{13}$ represents an alicyclic hydrocarbon group having a valency of (b+1); and b is an integer of 1 to 3.

In the above formula (III-3), $R^{14}$ represents a hydrogen atom or a methyl group; and $R^{15}$, $R^{16}$, $R^{17}$ and $R^{18}$ represent a group that forms a structure represented by the above formula (iii) together with the carbon atoms to which $R^{15}$, $R^{16}$, $R^{17}$ and $R^{18}$ each bond.

In the above formula (iii), A represents an alicyclic structure having 3 to 20 carbon atoms, a lactone structure having 3 to 20 carbon atoms, a cyclic carbonate structure having 3 to 20 carbon atoms, or a sultone structure having 3 to 20 carbon atoms; and d is an integer of 1 to 3.

In the above formula (III-4), $R^{14}$ is as defined in the above formula (III-3); $R^{19}$ represents a monovalent organic group; p is an integer of 0 to 3, wherein in a case where $R^{19}$ is present in a plurality of number, a plurality of $R^{19}$s are identical or different; and q is an integer of 1 to 3, wherein p and q satisfy p+q≤5.

It is preferred that $R^{L2}$ represents a methyl group in light of the copolymerizability of a monomer that gives the structural unit (III-1) or (III-2).

The divalent acid-labile group represented by E is a group which allows the cleavage of an oxygen-carbon bond between E and the ester group to which E bonds by an acid.

Such a group is exemplified by a 2,2-propanediyl group, a 2,2-butanediyl group, a 2,3-butanediyl group, and the like. Among these, a 2,2-propanediyl group is preferred.

Examples of the alicyclic hydrocarbon group having a valency of (b+1) represented by $R^{12}$ include:

divalent (i.e., b=1) alicyclic hydrocarbon groups such as a 1,3-adamantanediyl group, a 1,2-adamantanediyl group, a 2,5-norbornanediyl group and a 1,4-cyclohexanediyl group;

trivalent (i.e., b=2) alicyclic hydrocarbon groups such as a 1,3,5-adamantanetriyl group, a 1,2,3-adamantanetriyl group, a 2,3,5-norbornanetriyl group and a 1,3,4-cyclohexanetriyl group; and the like. Among these, a 1,3-adamantanetriyl group, and a 1,3,5-adamantanetriyl group are preferred, and a 1,3-adamantanetriyl group is more preferred.

Examples of the divalent hydrocarbon group which may be represented by L include:

alkanediyl groups such as a 2,2-propanediyl group, a 2,2-butanediyl group and a 2,3-butanediyl group;

cycloalkanediyl groups such as a 1,2-cyclopentanediyl group and a 1,2-cyclohexanediyl group; and the like. Among these, alkanediyl groups are preferred, and a 2,2-propanediyl group is more preferred.

Examples of the alicyclic hydrocarbon group having a valency of (b+1) represented by $R^{13}$ include groups identical to those exemplified in connection with the alicyclic hydrocarbon group having a valency of (b+1) represented by $R^{12}$, and the like.

Preferably, b is 1 or 2, and more preferably 1.

It is preferred that $R^{14}$ represents a hydrogen atom in light of the copolymerizability of a monomer that gives the structural unit (III).

Examples of the alicyclic structure which may be represented by A include monocyclic structures such as a cyclopentane structure and a cyclohexane structure; polycyclic structures such as a norbornane structure and an adamantane structure; and the like. Among these, a cyclohexane structure and an adamantane structure are preferred, and a cyclohexane structure is more preferred.

Preferably, d is 1 or 2, and more preferably 1.

The monovalent organic group represented by $R^{19}$ is exemplified by a monovalent linear hydrocarbon group having 1 to 12 carbon atoms, a monovalent alicyclic hydrocarbon group having 3 to 20 carbon atoms, a monovalent aromatic hydrocarbon group having 6 to 20 carbon atoms, a monovalent oxygen atom-containing organic group, a monovalent nitrogen atom-containing organic group, and the like.

Examples of the monovalent linear hydrocarbon group include a methyl group, an ethyl group, a n-propyl group, an i-propyl group, a n-butyl group, a 2-methylpropyl group, a 1-methylpropyl group, a t-butyl group, a n-pentyl group, a n-hexyl group, a n-decyl group, and the like.

Examples of the monovalent alicyclic hydrocarbon group include a cyclopentyl group, a cyclohexyl group, a cyclooctyl group, a norbornyl group, an adamantyl group, and the like.

Examples of the monovalent aromatic hydrocarbon group include a phenyl group, an o-tolyl group, a m-tolyl group, a p-tolyl group, a 2,4-xylyl group, a 2,6-xylyl group, a 3,5-xylyl group, a mesityl group, an o-cumenyl group, a m-cumenyl group, a p-cumenyl group, a benzyl group, a phenethyl group, a 1-naphthyl group, a 2-naphthyl group, and the like.

Examples of the monovalent oxygen atom-containing organic group include:

a carboxyl group;

linear or branched hydroxyalkyl groups having 1 to 8 carbon atoms such as a hydroxymethyl group, a 1-hydroxyethyl group and a 2-hydroxyethyl group;

hydroxycycloalkyl groups having 3 to 8 carbon atoms such as a 3-hydroxycyclopentyl group and a 4-hydroxycyclohexyl group;

linear or branched alkoxy groups having 1 to 8 carbon atoms such as a methoxy group and an ethoxy group;

cycloalkyloxy groups such as a cyclopentyloxy group and a cyclohexyloxy group;

linear alkoxycarbonyloxy groups having 2 to 9 carbon atoms such as a methoxycarbonyloxy group and an ethoxycarbonyloxy group;

linear or branched (1-alkoxyalkoxy)alkyl groups having 3 to 11 carbon atoms such as a (1-methoxyethoxy)methyl group and a (1-ethoxyethoxy)methyl group;

(1-cycloalkyloxyalkoxy)alkyl groups having 5 to 11 carbon atoms such as a (1-cyclopentyloxyethoxy)methyl group and a (1-cyclohexyloxyethoxy)methyl group;

linear or branched alkoxycarbonyloxyalkyl groups having 3 to 10 carbon atoms such as a methoxycarbonyloxymethyl group and an ethoxycarbonyloxymethyl group;

cycloalkyloxycarbonyloxyalkyl groups having 5 to 10 carbon atoms such as a cyclopentyloxycarbonyloxymethyl group and a cyclohexyloxycarbonyloxymethyl group; and the like.

Examples of the monovalent nitrogen atom-containing organic group include:

a cyano group;

linear or branched cyanoalkyl groups having 2 to 9 carbon atoms such as a cyanomethyl group, a 1-cyanoethyl group and a 2-cyanoethyl group;

cyanocycloalkyl groups having 4 to 9 carbon atoms such as a 3-cyanocyclopentyl group and a 4-cyanocyclohexyl group; and the like.

Among these, $R^{19}$ represents preferably a monovalent linear hydrocarbon group, and more preferably a methyl group, an ethyl group, a n-propyl group and an i-propyl group in light of an improvement of the rectangularity of the pattern.

Preferably, p is 0 to 2, more preferably 0 or 1, and still more preferably 0, and q is preferably 1 or 2, and more preferably 1.

Examples of the structural units (III-1) to (III-4) include structural units represented by the following formulae.

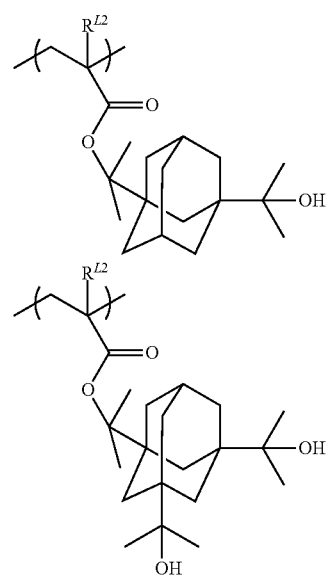

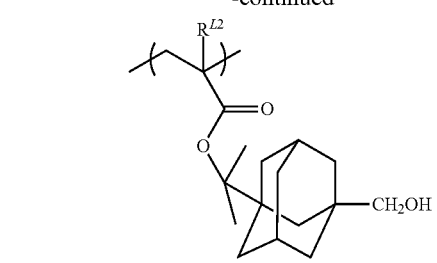
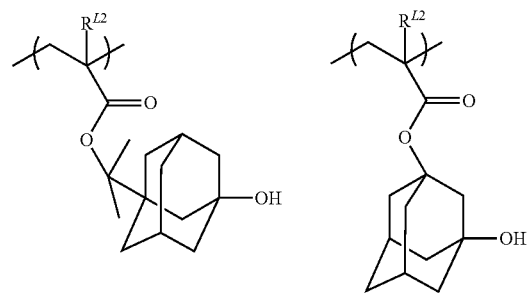
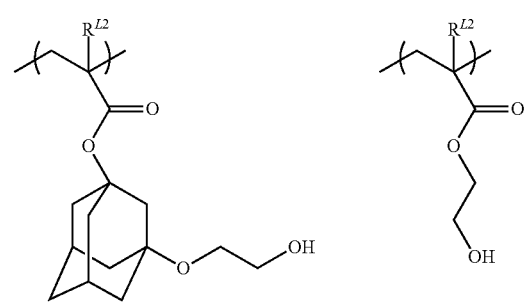
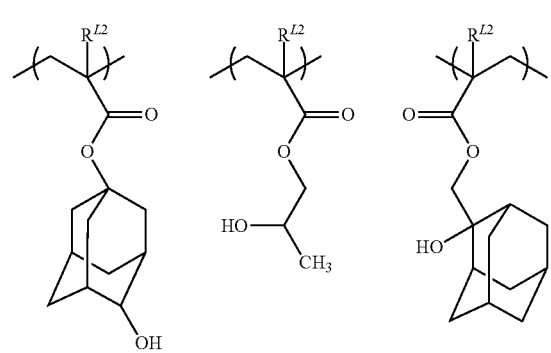
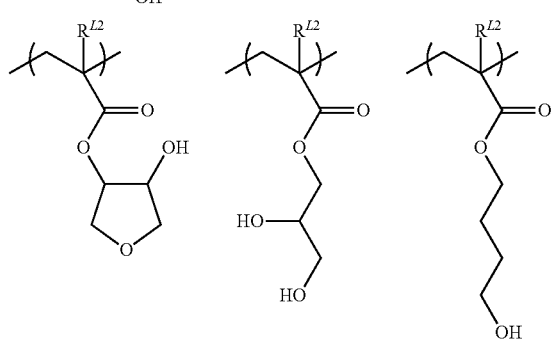
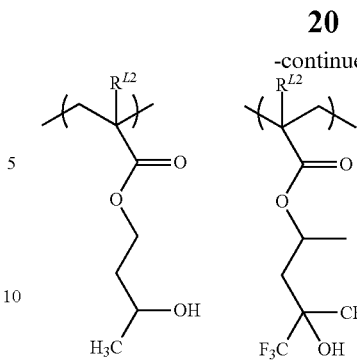
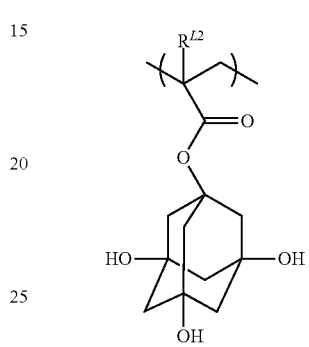
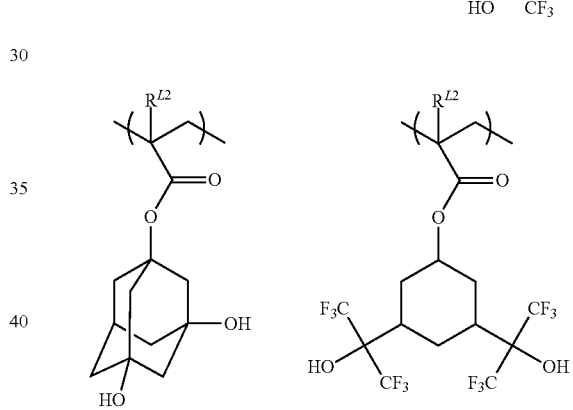
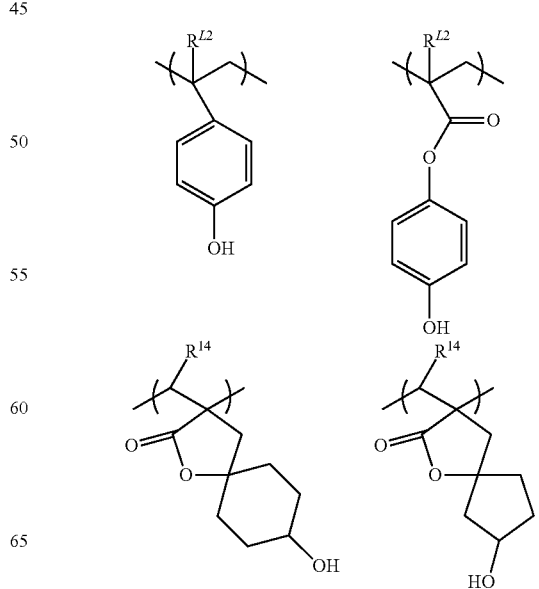
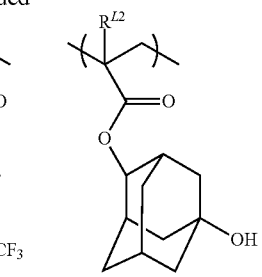
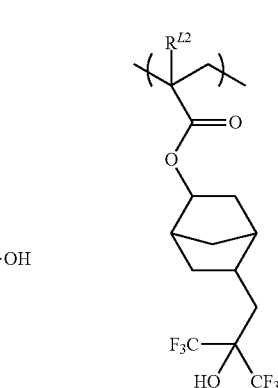
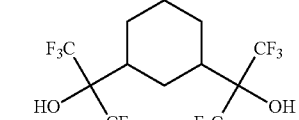
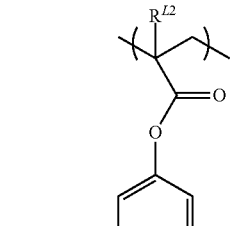
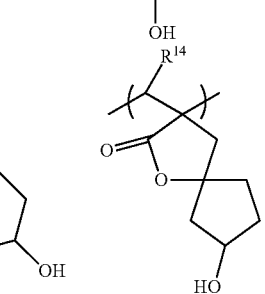

-continued

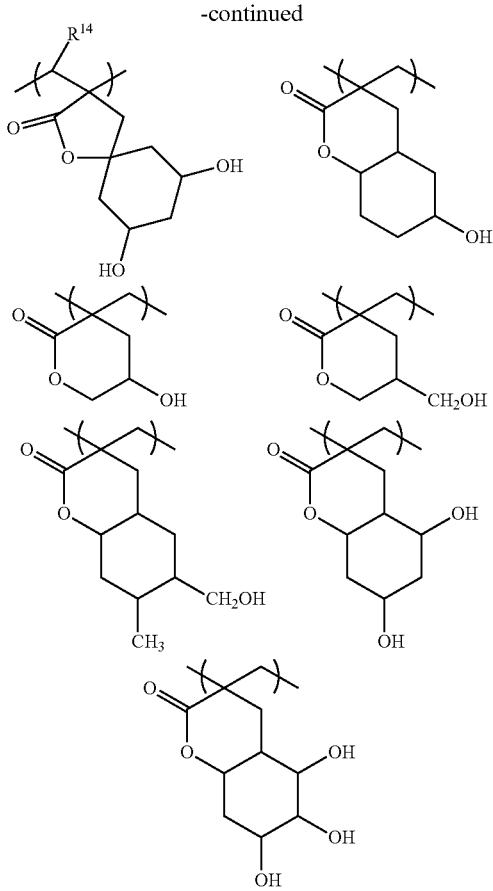

In the above formulae, $R^{L2}$ is as defined in the above formulae (III-1) and (III-2); and $R^{14}$ is as defined in the above formulae (III-3) and (III-4).

Among these, a structural unit derived from hydroxystyrene and a structural unit derived from 8-hydroxy-3-methylene-1-oxaspiro[4.5]decan-2-one are preferred.

The proportion of the structural unit (III) with respect to the total structural units constituting the polymer (A) is preferably no greater than 90 mol %, more preferably no less than 1 mol % and no greater than 80 mol %, and still more preferably no less than 2 mol % and no greater than 75 mol %. When the proportion of the structural unit (III) is greater than the abovementioned upper limit, a contrast attained after the development may be reduced, and therefore the pattern formability of the photoresist composition may be deteriorated.

Other Structural Unit

The polymer (A) may include other structural unit(s) in addition to the structural units (I) to (III). The other structural unit is exemplified by a structural unit that includes a non-acid-dissociable alicyclic hydrocarbon group, a structural unit that includes a polar group other than the hydroxy group such as a carboxy group and a sulfonamide group, and the like. The proportion of the other structural unit(s) with respect to the total structural units constituting the polymer (A) is typically no greater than 30 mol %, and preferably no greater than 20 mol %.

The content of the polymer (A) in the photoresist composition with respect to the total solid content is preferably no less than 70% by mass, and more preferably no less than 75% by mass. When the content of the polymer (A) is less than the abovementioned lower limit, the pattern formability of the photoresist composition may be deteriorated. It is to be noted that the photoresist composition may contain one, or two or more types of the polymer (A).

Synthesis Method of Polymer (A)

The polymer (A) can be synthesized in accordance with a conventional method such as radical polymerization, using a monomer that gives a structural unit that includes an acid-labile group, and the like. Examples of the synthesis method includes: a method including adding a solution containing a monomer and a radical initiator dropwise to a solution containing a reaction solvent or a monomer to permit a polymerization reaction; a method including separately adding a solution containing a monomer and a solution containing a radical initiator dropwise to a solution containing a reaction solvent or a monomer to permit a polymerization reaction; a method including separately adding a plurality of kinds of solutions containing each monomer, and a solution containing a radical initiator dropwise to a solution containing a reaction solvent or a monomer to permit a polymerization reaction; and the like.

The reaction temperature in the polymerization may be appropriately predetermined in accordance with the radical initiator species; and the reaction temperature is typically 30° C. to 180° C., preferably 40° C. to 160° C., and more preferably 50° C. to 140° C. The time period of the dropwise addition may vary depending on the reaction temperature, the type of the radical initiator, the monomer to be reacted and the like, and is typically 30 min to 8 hours, preferably 45 min to 6 hours, and more preferably 1 hour to 5 hours. In addition, a total reaction time period including the time period of dropwise addition is typically 30 min to 8 hours, preferably 45 min to 7 hours, and more preferably 1 hour to 6 hours.

Examples of the radical initiator include 2,2'-azobisisobutyronitrile (AIBN), 2,2'-azobis(4-methoxy-2,4-dimethylvaleronitrile), 2,2'-azobis(2-cyclopropylpropionitrile), 2,2'-azobis(2,4-dimethylvaleronitrile), dimethyl 2,2'-azobisisobutyrate, and the like. These radical initiators may be used as a mixture of two or more types thereof.

The solvent which may be used in the polymerization is not limited as long as it does not inhibit the polymerization of each monomer and is capable of dissolving the monomer. The solvent is exemplified by an alcohol solvent, a ketone solvent, an amide solvent, an ester solvent, a lactone solvent, a nitrile solvent, and the like. These solvents may be used in combination of two or more types thereof.

The polymer obtained by the polymerization reaction may be recovered using a reprecipitation technique. Alcohol solvents and the like may be used as a reprecipitation solvent.

In the polymerization reaction for the synthesis of the polymer (A), a molecular weight modifier may be used for adjusting the molecular weight. Examples of the molecular weight modifier include halogenated hydrocarbons such as chloroform and carbon tetrabromide; mercaptans such as n-hexyl mercaptan, n-octyl mercaptan, n-dodecyl mercaptan, t-dodecyl mercaptan, and thioglycolic acid; xanthogens such as dimethyl xanthogen sulfide and diisopropyl xanthogen disulfide; terpinolene; an α-methylstyrene dimer; and the like.

The polystyrene equivalent weight average molecular weight (Mw) of the polymer (A) as determined by gel permeation chromatography (GPC) is preferably 1,000 to 30,000, and more preferably 2,000 to 25,000. When the Mw of the polymer (A) falls within the abovementioned range, the photoresist composition may be superior in lithography performances such as sensitivity.

The ratio (Mw/Mn) of the Mw to the polystyrene equivalent number average molecular weight (Mn) as determined by GPC of the polymer (A) is typically no less than 1 and no greater than 5, preferably no less than 1 and no greater than 3, and more preferably no less than 1 and no greater than 2.5. When the Mw/Mn falls within the abovementioned range, the photoresist composition may be superior in lithography performances such as sensitivity, and in etching resistance. It is to be noted that the Mw and the Mn of the polymer used herein are determined by GPC under the following conditions.

columns: G2000HXL×2, G3000HXL×1, and G4000HXL×1 (manufactured by Tosoh Corporation)
    elution solvent: tetrahydrofuran
    column temperature: 40° C.
    flow rate: 1.0 mL/min
    sample concentration: 1.0% by mass
    amount of injected sample: 100 μL.
    detector: differential refractometer
    standard substance: mono-dispersed polystyrene (B) Compound The compound (B) is represented by the above formula (1). The compound (B) functions as an acid generating agent and/or a photodegradable base as described later in the section of "Compound (1)", due to the structure thereof. In either case where the compound (B) is used as the acid generating agent or as the photodegradable base, the resolving ability and LWR performance of the photoresist composition that contains the compound (B) may be improved. In a case where the compound (B) is used as the photodegradable base, it is preferred that the photoresist composition contains other acid generating agent.

In the above formula (1), $R^1$ represents a hydrogen atom or a monovalent acid-labile group; $R^2$ represents an alicyclic hydrocarbon group having 3 to 20 carbon atoms and a valency of (m+1); m is an integer of 2 to 5; $R^3$ and $R^4$ each independently represent a hydrogen atom, a fluorine atom, a monovalent hydrocarbon group having 1 to 20 carbon atoms or a monovalent fluorinated hydrocarbon group having 1 to 20 carbon atoms; n is an integer of 0 to 5, wherein a plurality of $R^1$s are identical to or different from each other, a plurality of $R^3$s, in a case where $R^3$ is present in a plurality of number, are identical to or different from each other, and a plurality of $R^4$s, in a case where $R^4$ is present in a plurality of number, are identical to or different from each other, and wherein at least two of the plurality of $R^1$s optionally taken together represent a ring structure by binding with each other, together with a plurality of oxygen atoms that bond to $R^1$ and the carbon atom(s) constituting $R^2$ and bonding to these oxygen atoms; and $M^+$ represents a monovalent radiation-degradable onium cation.

In a case where $R^1$ represents a hydrogen atom, the compound (B) includes a hydroxy group. Alternatively, in a case where $R^1$ represents a monovalent acid-labile group, the compound (B) generates a hydroxy group by an action of an acid generated upon an exposure. In the case where $R^1$ represents a hydrogen atom, the interaction of the hydroxy group with a polymer component is enhanced, and therefore the dispersibility of the compound (B) in the formed resist film may be increased. In the case where $R^1$ represents an acid-labile group, the solubility of the compound (B) in a solvent may be increased, leading to the ease of the preparation of the photoresist composition. As a result, an advantage may be exhibited that the dispersibility of the compound (B) in the formed resist film is increased. Even in this case, since the acid-labile group is dissociated by the action of the acid generated upon the exposure, and a hydroxy group is generated, the compound (B) can exhibit the effect of properly reducing an acid diffusion length attributed to the hydroxy group, and the like.

Examples of the monovalent acid-labile group which may be represented by $R^1$ include a t-butyl group, a t-amyl group, a methoxymethyl group, an ethoxyethyl group, and the like. In this regard, the "acid-labile group" represented by $R^1$ means a group that substitutes a hydrogen atom of a hydroxy group and is dissociated in the presence of an acid to give a hydroxy group.

Examples of the alicyclic hydrocarbon group having 3 to 20 carbon atoms and a valency of (m+1) represented by $R^2$ include monocyclic alicyclic hydrocarbons such as cyclopropane, cyclobutane, cyclopentane and cyclohexane; groups obtained by eliminating (m+1) hydrogen atoms from polycyclic alicyclic hydrocarbons such as norbornane and adamantane; and the like. Among these, polycyclic alicyclic hydrocarbon groups are preferred, and a group obtained by eliminating (m+1) hydrogen atoms from norbornane is more preferred. In addition, m oxygen atoms and the carbon atoms in $R^2$ preferably bond such that each of the m oxygen atoms bonds to each different carbon atom included in $R^2$.

Examples of the monovalent hydrocarbon group having 1 to 20 carbon atoms which may be represented by $R^3$ and $R^4$ include a methyl group, an ethyl group, a n-propyl group, an i-propyl group, a n-butyl group, an i-butyl group, a sec-butyl group, a t-butyl group, a n-hexyl group, a n-decyl group, and the like.

Examples of the monovalent fluorinated hydrocarbon group having 1 to 20 carbon atoms which may be represented by $R^3$ and $R^4$ include a fluoromethyl group, a difluoromethyl group, a trifluoromethyl group, a fluoroethyl group, a difluoroethyl group, a trifluoroethyl group, a perfluoroethyl group, a perfluoro-n-propyl group, a hexafluoro-i-propyl group, a perfluorobutyl group, a perfluoropentyl group, a perfluorohexyl group, a perfluorooctyl group, a perfluorodecyl group, and the like.

Preferably, m is an integer of 2 to 4, and more preferably 2.

Preferably, n is an integer of 0 to 2, and more preferably 2.

Examples of the ring structure optionally taken together represented by the at least two of the plurality of $R^1$s by binding with each other, together with a plurality of oxygen atoms that bond to $R^1$ and the carbon atom(s) constituting $R^2$ and bonding to these oxygen atoms include: a ring structure in which at least two $R^1$s bind with each other to form a group represented by $*-(CR_2)_a-*$, wherein R represents a hydrogen atom or an alkyl group having 1 to 10 carbon atoms; a is an integer of 1 to 4, wherein in a case where R is present in a plurality of number, a plurality of Rs are identical or different; and * denotes a site of binding to the oxygen atom; and the like. It is to be noted that in a case where each of the plurality of oxygen atoms bonds to a different carbon atom in $R^2$ to form the ring structure, other carbon atom(s) constituting $R^2$ may be included between the carbon atoms to which the plurality of oxygen atoms bond.

Examples of the alkyl group having 1 to 10 carbon atoms which may be represented by R include a methyl group, an ethyl group, a propyl group, a butyl group, and the like.

It is preferred that R represents a hydrogen atom, a methyl group, or an ethyl group.

Preferably, a represents 1.

Examples of the ring structure wherein m is 2 and a is 2 to 4 include a 1,4-dioxacyclohexane structure, a 1,4-dioxacycloheptane structure and, a 1,5-dioxacyclooctane structure, and the like.

In a case where m is 2 and a is 1 (in the case of the crosslinking of two oxygen atoms via one carbon atom), it is preferred $(R^1O)_m-$ in the above formula (1) is represented by the above formula (Y).

In the above formula (Y), R' and R" each independently represent a hydrocarbon group having 1 to 10 carbon atoms, wherein R' and R" optionally taken together represent a ring structure by binding with each other, together with the carbon atom to which R' and R" bond.

Examples of the hydrocarbon group having 1 to 10 carbon atoms represented by R' or R" include a methyl group, an ethyl group, a n-propyl group, an i-propyl group, a n-butyl group, a pentyl group, a hexyl group, an octyl group, and the like. Among these, a methyl group, an ethyl group and a n-propyl group are preferred, and a methyl group is more preferred.

Examples of the ring structure optionally taken together represented by R' and R" by binding with each other, together with the carbon atom to which R' and R" bond include:

monocyclic saturated hydrocarbon structures such as a cyclopropane structure, a cyclobutane structure, a cyclopentane structure, a cyclohexane structure, a cycloheptane structure, a cyclooctane structure, a cyclodecane structure, a methylcyclohexane structure and an ethylcyclohexane structure;

monocyclic unsaturated hydrocarbon structures such as a cyclobutene structure, a cyclopentene structure, a cyclohexene structure, a cycloheptene structure, a cyclooctene structure, a cyclodecene structure, a cyclopentadiene structure, a cyclohexadiene structure, a cyclooctadiene structure and a cyclodecadiene structure;

polycyclic saturated hydrocarbon structures such as a bicyclo[2.2.1]heptane structure, a bicyclo[2.2.2]octane structure, a tricyclo[5.2.1.0$^{2,6}$]decane structure, a tricyclo[3.3.1.1$^{3,7}$]decane structure, a tetracyclo[6.2.1.1$^{3,6}$.0$^{2,7}$]dodecane structure, a norbornane structure and an adamantane structure;

polycyclic unsaturated hydrocarbon structures such as a bicyclo[2.2.1]heptene structure, a bicyclo[2.2.2]octene structure, a tricyclo[5.2.1.0$^{2,6}$]decene structure, a tricyclo[3.3.1.1$^{3,7}$]decene structure and a tetracyclo[6.2.1.1$^{3,6}$.0$^{2,7}$]dodecene structure; and the like.

The ring structure optionally taken together represented by R' and R" by binding with each other, together with the carbon atom to which R' and R" bond is preferably a cyclohexane structure and an adamantane structure.

In a case where three or more oxygen atoms are crosslinked via one carbon atom, the *—(CR$_2$)$_a$—* group formed in the case of m being 3, for example, is exemplified by a methylmethanetriyl group, an ethylmethanetriyl group, and the like, and these groups form a cyclic ortho ester structure together with three oxygen atoms that bond to these groups and the carbon atom that bonds to these oxygen atoms. Alternatively, the *—(CR$_2$)$_a$—* group formed in the case of m being 4, for example, is exemplified by a methanetetrayl group and the like, and these groups form a cyclic ortho carbonic acid ester structure together with four oxygen atoms that bond to these groups and the carbon atom that bonds to these oxygen atoms.

The compound represented by the above formula (1) is represented preferably by the above formula (1-I), and more preferably by the above formula (1-i).

In the above formula (1-I), R$^2$ represents a trivalent alicyclic hydrocarbon group having 3 to 20 carbon atoms; R$^3$, R$^4$, n and M$^+$ are as defined in the above formula (1); and R' and R" are as defined in the above formula (Y). In the above formula (1-i), n and M$^+$ are as defined in the above formula (1), and R' and R" are as defined in the above formula (Y).

Examples of the perfluoroalkyl group which may be represented by R$^3$ and R$^4$ in the above formula (1-i) include a trifluoromethyl group, a perfluoroethyl group, a perfluoro-n-propyl group, a perfluorobutyl group, a perfluoropentyl group, a perfluorohexyl group, a perfluorooctyl group, a perfluorodecyl group, and the like.

Examples of the compound represented by the above formula (1) include compounds represented by the following formulae (1-1) to (1-6), and the like.

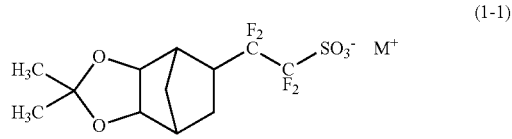
(1-1)

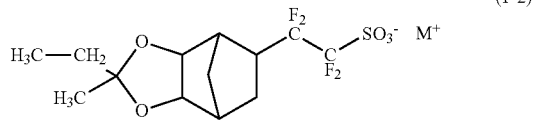
(1-2)

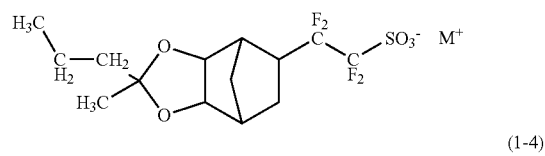
(1-3)

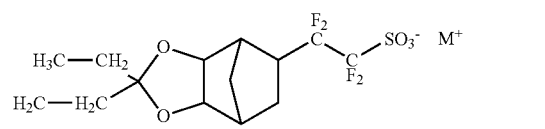
(1-4)

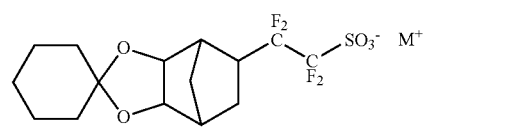
(1-5)

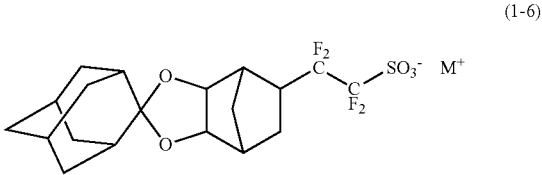
(1-6)

In the above formulae (1-1) to (1-6), M$^+$ is as defined in the above formula (1).

Among these, the compound represented by the above formula (1-1) is preferred.

M$^+$ represents a monovalent radiation-degradable onium cation. The radiation-degradable onium cation is degraded upon the irradiation with a radioactive ray to generate a proton, resulting in the generation of a sulfonic acid from the compound represented by the above formula (1). M$^+$ preferably represents a sulfonium cation or an iodonium cation.

The sulfonium cation is preferably a cation represented by the above formula (2).

In the above formula (2), R$^5$ represents a fluorine atom, a hydroxy group, an alkyl group having 1 to 10 carbon atoms, an alkoxy group having 1 to 10 carbon atoms, an alkoxycarbonyl group having 2 to 11 carbon atoms, or an alkylsulfonyl group having 1 to 10 carbon atoms; j is an integer of 0 to 9, wherein in a case where j is no less than 2, a plurality of R$^5$s are identical or different; R$^6$ and R$^7$ each independently represent an alkyl group having 1 to 10 carbon atoms or an aryl group having 6 to 20 carbon atoms, wherein a part or all of hydrogen atoms included in the alkyl group and the aryl group are unsubstituted or substituted, and wherein R$^6$ and R$^7$ optionally taken together represent a ring structure having 2 to 10 carbon atoms by binding with each other, together with the sulfur atom to which $R^6$ and $R^7$ bond; and k is an integer of 0 to 2.

Examples of the alkyl group having 1 to 10 carbon atoms which may be represented by $R^5$ include a methyl group, an ethyl group, a propyl group, a butyl group, and the like. Among these, a methyl group is preferred.

Examples of the alkoxy group having 1 to 10 carbon atoms which may be represented by $R^5$ include a methoxy group, an ethoxy group, a propoxy group, a butoxy group, and the like. Among these, a methoxy group is preferred.

Examples of the alkoxycarbonyl group having 2 to 11 carbon atoms which may be represented by $R^5$ include: linear alkoxycarbonyl groups such as a methoxycarbonyl group, an ethoxycarbonyl group, a n-propoxycarbonyl group, a n-butoxycarbonyl group and a n-pentyloxycarbonyl group; branched alkoxycarbonyl groups such as an i-propoxycarbonyl group, a 2-methylpropoxycarbonyl group and a 1-methylpropoxycarbonyl group; and the like. Among these, a methoxycarbonyl group, an ethoxycarbonyl group, and a n-butoxycarbonyl group are preferred.

Examples of the alkylsulfonyl group having 1 to 10 carbon atoms which may be represented by $R^5$ include: linear alkylsulfonyl groups such as a methylsulfonyl group, an ethylsulfonyl group, a n-propylsulfonyl group and a n-butylsulfonyl group; branched alkylsulfonyl groups such as a t-butylsulfonyl group, a neopentylsulfonyl group and a 2-ethylhexylsulfonyl group; cycloalkylsulfonyl groups such as a cyclopentylsulfonyl group and a cyclohexylsulfonyl group; and the like. Among these, a methylsulfonyl group, an ethylsulfonyl group, a n-propylsulfonyl group, a n-butylsulfonyl group, a cyclopentylsulfonyl group and a cyclohexylsulfonyl group are preferred.

Preferably, j is an integer of 0 to 2.

Examples of the alkyl group having 1 to 10 carbon atoms which may be represented by $R^6$ or $R^7$ include groups similar to the alkyl groups having 1 to 10 carbon atoms exemplified in connection with $R^5$ as described above, and the like.

Examples of the aryl group having 6 to 20 carbon atoms which may be represented by $R^6$ or $R^7$ include a phenyl group, a naphthyl group, and the like.

Examples of the substituent optionally included in the alkyl group and the aryl group include a hydroxy group, a cyano group, a halogen atom, an alkoxy group, an acyl group, an acyloxy group, an alkoxycarbonyl group, an alkoxycarbonyloxy group, and the like.

The ring structure optionally taken together represented by $R^6$ and $R^7$ by binding with each other is preferably a structure that includes a 5-membered ring or a 6-membered ring, and more preferably a tetrahydrothiophene ring structure.

Preferably, k is 1 or 2.

Examples of the radiation-degradable onium cation represented by the above formula (2) include cations represented by the following formulae (2-1) to (2-7), and the like.

(2-1)

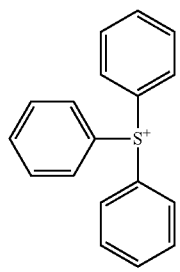

(2-2)

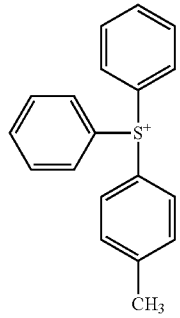

(2-3)

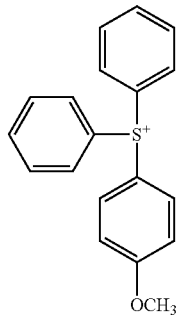

(2-4)

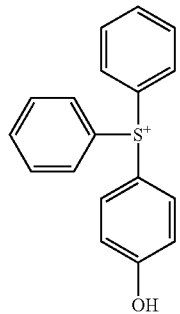

(2-5)

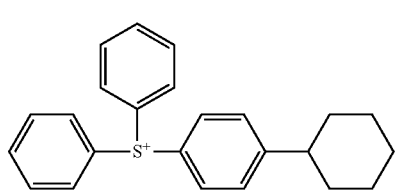

(2-6)

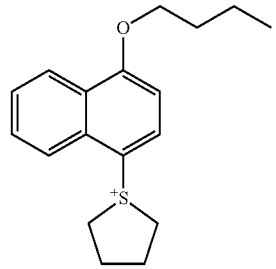

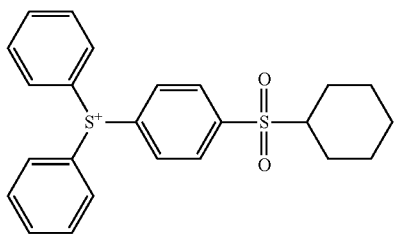

Among these, the cation represented by the above formula (2-1) is preferred.

Synthesis Method of Compound (B)

The compound (B) can be synthesized, for example, in accordance with the scheme represented by the following chemical equation.

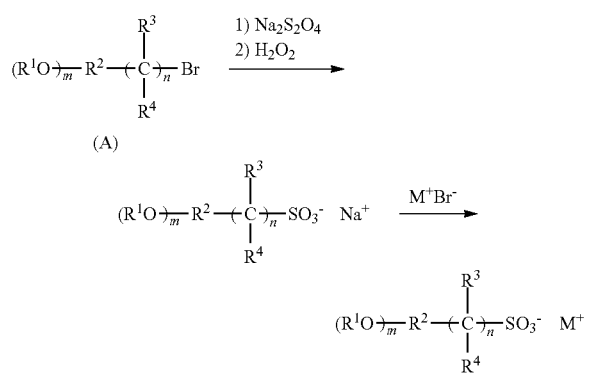

In the above chemical equation, $R^1$ to $R^4$, m, n and $M^+$ are as defined in the above formula (1).

The compound represented by the above formula (A), which is a bromide corresponding to the compound (B), is reacted with sodium dithionite to obtain a product, and the product is oxidized with hydrogen peroxide to obtain a sulfonic acid sodium salt. The compound (B) can be obtained from the sulfonic acid sodium salt and a salt that includes a monovalent radiation-degradable onium cation represented by $M^+$.

In regard to the compound represented by the above formula (A), in a case where m is 2 and $R^2$ is a norbornanetriyl group, a diol compound and a cyclic acetal form derived therefrom can be synthesized, for example, in accordance with the following scheme.

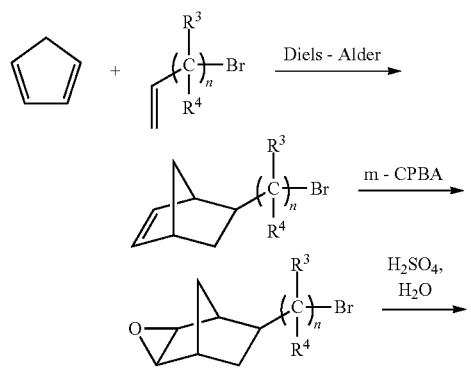

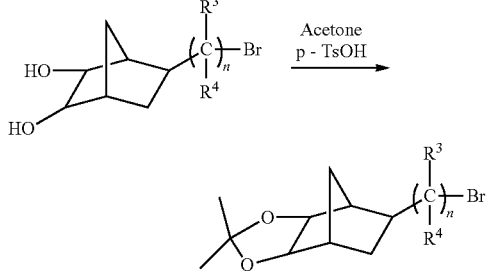

In the above chemical equation, $R^3$, $R^4$ and n are as defined in the above formula (1).

A bromo-substituted norbornene compound is obtained by subjecting cyclopentadiene and a bromo-substituted olefin to a Diels-Alder reaction. The diol compound can be obtained by epoxidizing the double bond of the compound with an oxidizing agent such as m-chloroperbenzoic acid (m-CPBA), followed by a treatment with an aqueous solution of an acid such as sulfuric acid. Moreover, the cyclic acetal form can be obtained by reacting the diol compound with a carbonyl compound such as acetone in the presence of an acid such as p-toluenesulfonic acid (p-TsOH).

Two or more types of the compounds (B), e.g., a compound (B) that functions as an acid generating agent and a compound (B) that functions as a photodegradable base, may be contained. When the two or more types of the compounds (B), e.g., the acid generating agent and the photodegradable base, are thus contained as the compound (B) in the photoresist composition, lithography performances such as a resolution and an LWR performance may be further improved through a synergistic effect of the acid generating agent and the photodegradable base.

In a case where the compound (B) functions as the acid generating agent, the content of the compound (B) with respect to 100 parts by mass of the polymer (A) is preferably no less than 0.1 parts by mass and no greater than 20 parts by mass, and more preferably no less than 0.5 parts by mass and no greater than 18 parts by mass. When the content of the compound (B) in the case of the compound (B) functioning as the acid generating agent is less than 0.1 parts by mass, the sensitivity and developability of the photoresist composition tends to be deteriorated. On the other hand, when the content of the compound (B) is greater than 20 parts by mass, the transparency to radioactive rays may be impaired, leading to difficulty of obtaining a desired resist pattern.

In a case where the compound (B) functions as the photodegradable base, the content of the compound (B) with respect to 100 parts by mass of the polymer (A) is preferably no less than 0.1 parts by mass and no greater than 15 parts by mass, and more preferably no less than 0.5 parts by mass and no greater than 12 parts by mass. When the content of the compound (B) in the case of the compound (B) functioning as the photodegradable base is less than 0.1 parts by mass, the effect of the improvement of the resolving ability and LWR performance of the photoresist composition tends to be diminished. On the other hand, when the content of the compound (B) is greater than 15 parts by mass, the transparency to radioactive rays may be impaired, leading to difficulty of obtaining a desired resist pattern.

(C) Fluorine Atom-Containing Polymer

The fluorine atom-containing polymer (C) is a polymer that contains a fluorine atom and has a content of fluorine atoms higher than a content of fluorine atoms of the polymer (A). When the photoresist composition contains the fluorine atom-containing polymer (C), the hydrophobicity of the resist film may be further improved, and in a case where an exposure through a liquid immersion medium is carried out, the elution of an acid generating agent, an acid diffusion control agent and the like contained in a resist film into the liquid immersion medium can be inhibited.

Exemplary modes of the fluorine atom-containing polymer (C) involve: a structure in which a fluorinated alkyl group bonds to a main chain of the fluorine atom-containing polymer (C); a structure in which a fluorinated alkyl group bonds to a side chain of the fluorine atom-containing polymer (C); a structure in which fluorinated alkyl groups bond to a main chain and a side chain of the fluorine atom-containing polymer (C); and the like.

Examples of the monomer that gives the structure in which a fluorinated alkyl group bonds to a main chain of the fluorine atom-containing polymer (C) include α-trifluoromethylacrylate compounds, β-trifluoromethylacrylate compounds, α,β-trifluoromethylacrylate compounds, compounds derived by substituting a hydrogen of one or more types of vinyl moieties with a fluorinated alkyl group such as a trifluoromethyl group, and the like.

Examples of the monomer that gives the structure in which a fluorinated alkyl group bonds to a side chain of the fluorine atom-containing polymer (C) include alicyclic olefin compounds having a fluorinated alkyl group as a side chain such as norbornene having a fluorinated alkyl group as a side chain, compounds derived from (meth)acrylic acid by introducing a fluorinated alkyl group thereto as a side chain, compounds derived from one or more types of olefins by introducing a fluorinated alkyl group to a side chain (a moiety excluding a double bond) thereof, and the like.

Examples of the monomer that gives the structure in which fluorinated alkyl groups bond to a main chain and a side chain of the fluorine atom-containing polymer (C) include: compounds derived from α-trifluoromethylacrylic acid, β-trifluoromethylacrylic acid, α,β-trifluoromethylacrylic acid or the like by introducing a fluorinated alkyl group thereto as a side chain; compounds derived from compounds having a vinyl group as a main chain structure by introducing fluorinated alkyl groups to the main chain and the side chain thereof; and the like.

The fluorine atom-containing polymer (C) preferably has a structural unit (IV) represented by the following formula (5) and/or a structural unit (V) represented by the following formula (6). In addition, the fluorine atom-containing polymer (C) may have a structural unit other than the structural unit (IV) and the structural unit (V). It is to be noted that the fluorine atom-containing polymer (C) may have two or more types of each structural unit. Hereinafter, each structural unit will be described in detail.

Structural Unit (IV)

The structural unit (IV) is represented by the following formula (5).

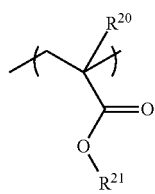

(5)

In the above formula (5), $R^{20}$ represents a hydrogen atom, a fluorine atom, a methyl group or a trifluoromethyl group; and $R^{21}$ represents a linear or branched alkyl group having 1 to 6 carbon atoms and having a fluorine atom or a monovalent alicyclic group having 4 to 20 carbon atoms and having a fluorine atom, wherein a part or all of hydrogen atoms included in the alkyl group and the alicyclic group are unsubstituted or substituted.

In regard to the linear or branched alkyl group having 1 to 6 carbon atoms and having a fluorine atom which may be represented by $R^{21}$, examples of the linear or branched alkyl group having 1 to 6 carbon atoms include a methyl group, an ethyl group, a propyl group, a butyl group, and the like.

In regard to the monovalent alicyclic group having 4 to 20 carbon atoms and having a fluorine atom which may be represented by $R^{21}$, examples of the monovalent alicyclic group having 4 to 20 carbon atoms include a cyclopentyl group, a cyclopentylpropyl group, a cyclohexyl group, a cyclohexylmethyl group, a cycloheptyl group, a cyclooctyl group, a cyclooctylmethyl group, and the like.

Examples of the monomer that gives the structural unit (IV) include trifluoromethyl (meth)acrylate, 2,2,2-trifluoroethyl (meth)acrylate, perfluoroethyl (meth)acrylate, perfluoro-n-propyl (meth)acrylate, perfluoro-i-propyl (meth)acrylate, perfluoro-n-butyl (meth)acrylate, perfluoro-i-butyl (meth)acrylate, perfluoro-t-butyl (meth)acrylate, perfluorocyclohexyl (meth)acrylate, 2-(1,1,1,3,3,3-hexafluoro)propyl (meth)acrylate, 1-(2,2,3,3,4,4,5,5-octafluoro)pentyl (meth)acrylate, 1-(2,2,3,3,4,4,5,5-octafluoro)hexyl (meth)acrylate, perfluorocyclohexylmethyl (meth)acrylate, 1-(2,2,3,3,3-pentafluoro)propyl (meth)acrylate, 1-(2,2,3,3,4,4,4-heptafluoro)butyl (meth)acrylate, 1-(3,3,4,4,5,5,6,6,7,7,8,8,9,9,10,10,10-heptadecafluoro)decyl (meth)acrylate, 1-(5-trifluoromethyl-3,3,4,4,5,6,6,6-octafluoro)hexyl (meth)acrylate, and the like. Among these, 2,2,2-trifluoroethyl (meth)acrylate is preferred.

The proportion of the structural unit (IV) in the fluorine atom-containing polymer (C) with respect to the total structural units constituting the fluorine atom-containing polymer (C) is preferably 5 mol % to 50 mol %, and more preferably 5 mol % to 40 mol %.

Structural Unit (V)

The structural unit (V) is represented by the following formula (6).

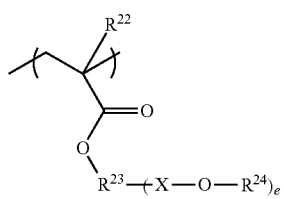

(6)

In the above formula (6), $R^{22}$ represents a hydrogen atom, a methyl group or a trifluoromethyl group; e is an integer of 1 to 3; $R^{23}$ represents a linking group having a valency of (e+1); X represents a divalent linking group having a fluorine atom; and $R^{24}$ represents a hydrogen atom or a monovalent organic group, wherein in a case where e is 2 or 3, a plurality of Xs are identical to or different from each other, and a plurality of $R^{24}$s are identical to or different from each other.

The linking group having a valency of (e+1) which may be represented by $R^{24}$ is exemplified by: a linear or branched hydrocarbon group having 1 to 30 carbon atoms; an alicyclic group having 3 to 30 carbon atoms, an aromatic group having 6 to 30 carbon atoms; or a group obtained by combining one of these groups with one or more types of group selected from the group consisting of an oxygen atom, a sulfur atom, an ether group, an ester group, a carbonyl group, an imino group and an amide group; and the like. In addition, the linking group having a valency of (e+1) may have a substituent.

Examples of the linear or branched hydrocarbon group having 1 to 30 carbon atoms include groups obtained by eliminating (e+1) hydrogen atoms from a hydrocarbon group such as methane, ethane, propane, butane, pentane, hexane, heptane, decane, icosane and triacontane, and the like.

Examples of the alicyclic group having 3 to 30 carbon atoms include groups obtained by eliminating (e+1) hydrogen atoms from:

a monocyclic saturated hydrocarbon such as cyclopropane, cyclobutane, cyclopentane, cyclohexane, cycloheptane, cyclooctane, cyclodecane, methylcyclohexane and ethylcyclohexane;

a monocyclic unsaturated hydrocarbon such as cyclobutene, cyclopentene, cyclohexene, cycloheptene, cyclooctene, cyclodecene, cyclopentadiene, cyclohexadiene, cyclooctadiene and cyclodecadiene;

a polycyclic saturated hydrocarbon such as bicyclo[2.2.1]heptane, bicyclo[2.2.2]octane, tricyclo[5.2.1.0$^{2,6}$]decane, tricyclo[3.3.1.1$^{3,7}$]decane, tetracyclo[6.2.1.1$^{3,6}$.0$^{2,7}$]dodecane and adamantane; or a polycyclic unsaturated hydrocarbon such as bicyclo[2.2.1]heptene, bicyclo[2.2.2]octene, tricyclo[5.2.1.0$^{2,6}$]decene, tricyclo[3.3.1.1$^{3,7}$]decene and tetracyclo[6.2.1.1$^{3,6}$.0$^{2,7}$]dodecene; and the like.

Examples of the aromatic group having 6 to 30 carbon atoms include: groups obtained by eliminating (e+1) hydrogen atoms from an aromatic hydrocarbon such as benzene, naphthalene, phenanthrene, anthracene, tetracene, pentacene, pyrene, picene, toluene, xylene, ethylbenzene, mesitylene and cumene; and the like.

The divalent linking group having a fluorine atom represented by X is exemplified by: a divalent linear hydrocarbon group having 1 to 20 carbon atoms and having a fluorine atom; a divalent linear hydrocarbon group having 1 to 20 carbon atoms and having a carbonyl group and a fluorine atom; and the like. Examples of the divalent linear hydrocarbon group having 1 to 20 carbon atoms and having a fluorine atom include groups represented by the following formulae (X-1) to (X-7), and the like.

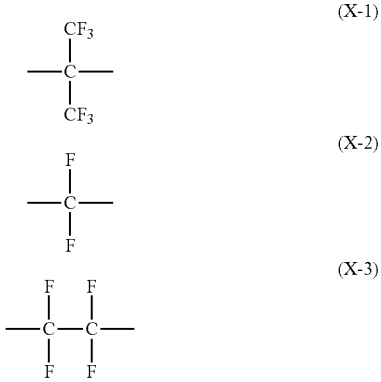

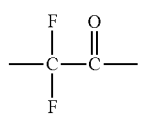

X preferably represents the group represented by the above formula (X-7).

Examples of the monovalent organic group which may be represented by R$^{24}$ include: linear or branched hydrocarbon groups having 1 to 30 carbon atoms; alicyclic groups having 3 to 30 carbon atoms; aromatic groups having 6 to 30 carbon atoms; groups obtained by combining one of these groups with one or more types of group selected from the group consisting of an oxygen atom, a sulfur atom, an ether group, an ester group, a carbonyl group, an imino group and an amide group; and the like.

Examples of the monomer that gives the structural unit (V) include (meth)acrylic acid 2-(1-ethoxycarbonyl-1,1-difluoro)butyl ester, (meth)acrylic acid (1,1,1-trifluoro-2-trifluoromethyl-2-hydroxy-3-propyl) ester, (meth)acrylic acid (1,1,1-trifluoro-2-trifluoromethyl-2-hydroxy-4-butyl) ester, (meth)acrylic acid (1,1,1-trifluoro-2-trifluoromethyl-2-hydroxy-5-pentyl) ester, (meth)acrylic acid (1,1,1-trifluoro-2-trifluoromethyl-2-hydroxy-4-pentyl) ester, (meth)acrylic acid 2-{[5-(1',1',1'-trifluoro-2'-trifluoromethyl-2'-hydroxy)propyl]bicyclo[2.2.1]heptyl}ester, and the like. Among these, (meth)acrylic acid 2-(1-ethoxycarbonyl-1,1-difluoro) butyl ester is preferred.

The proportion of the structural unit (V) in the fluorine atom-containing polymer (C) with respect to the total structural units constituting the fluorine atom-containing polymer (C) is preferably 5 mol % to 90 mol %, and more preferably 5 mol % to 80 mol %.

Other Structural Unit

The fluorine atom-containing polymer (C) may have, as other structural unit(s), the structural unit (I) for the purpose of improving etching resistance, the structural unit (II) for the purpose of improving solubility in a developer solution, and/or the like. It is to be noted that the fluorine atom-containing polymer (C) may have two or more types of the other structural unit.

The proportion of the other structural unit in the fluorine atom-containing polymer (C) with respect to the total structural units constituting the fluorine atom-containing polymer (C) is typically no greater than 90 mol %, preferably 5 mol % to 80 mol %, and more preferably 5 mol % to 75 mol %.

The content of the fluorine atom-containing polymer (C) with respect to 100 parts by mass of the polymer (A) is preferably 0.1 parts by mass to 20 parts by mass, and more preferably 1 part by mass to 10 parts by mass. When the content of the fluorine atom-containing polymer (C) is less than 0.1 parts by mass, the effect of the incorporation of the fluorine atom-containing polymer (C) may not be sufficiently exhibited. On the other hand, when the content of the fluorine atom-containing polymer (C) is, greater than 20 parts by mass, the water repellency of the resist surface becomes so great that a poor development may occur.

The content of fluorine atoms in the fluorine atom-containing polymer (C) with respect to the total amount of the fluorine atom-containing polymer (C) assumed to be 100% by mass is typically no less than 5% by mass, preferably 5% by mass to 50% by mass, and more preferably 5% by mass to 45% by mass. It is to be noted that the content of fluorine atoms can be determined by $^{13}$C-NMR. When the content of fluorine atoms in the fluorine atom-containing polymer (C) is higher than that of the polymer (A), the water repellency of the surface of a resist film formed from the photoresist composition that contains the fluorine atom-containing polymer (C) and the polymer (A) can be enhanced. As a result, it is unnecessary to separately provide an upper layer film in the liquid immersion lithography. In order to sufficiently exhibit the abovementioned effect, the difference between the content of fluorine atoms in the polymer (A) and the content of fluorine atoms in the fluorine atom-containing polymer (C) is preferably no less than 1% by mass, and more preferably no less than 3% by mass.

Synthesis Method of Fluorine Atom-Containing Polymer (C)

The fluorine atom-containing polymer (C) can be synthesized by, for example, polymerizing monomer(s) that give(s) each predetermined structural unit in an appropriate solvent using a radical polymerization initiator.

Examples of the solvent which may be used in the polymerization include:

alkanes such as n-pentane, n-hexane, n-heptane, n-octane, n-nonane and n-decane;

cycloalkanes such as cyclohexane, cycloheptane, cyclooctane, decalin and norbornane;

aromatic hydrocarbons such as benzene, toluene, xylene, ethylbenzene and cumene;

halogenated hydrocarbons such as chlorobutanes, bromohexanes, dichloroethanes, hexamethylene dibromide and chlorobenzene;

saturated carboxylic acid esters such as ethyl acetate, n-butyl acetate, i-butyl acetate and methyl propionate;

ketones such as acetone, 2-butanone, 4-methyl-2-pentanone and 2-heptanone;

ethers such as tetrahydrofuran, diethoxyethanes and diethoxyethanes;

alcohols such as methanol, ethanol, 1-propanol, 2-propanol and 4-methyl-2-pentanol; and the like. It is to be noted that these solvents may be used in combination of two or more types thereof.

The reaction temperature in the polymerization is typically 40° C. to 150° C., and preferably 50° C. to 120° C. The reaction time period is typically 1 hour to 48 hours, and preferably 1 hour to 24 hours.

The Mw of the fluorine atom-containing polymer (C) is preferably 2,000 to 10,000, and more preferably 2,500 to 7,000. When the Mw of the fluorine atom-containing polymer (C) is less than 2,000, attaining a sufficient receding contact angle may fail. On the other hand, when the Mw of the fluorine atom-containing polymer (C) is greater than 10,000, the developability of the resist formed tends to be impaired.

The ratio (Mw/Mn) of the Mw to the polystyrene equivalent number average molecular weight (Mn) determined by GPC of the fluorine atom-containing polymer (C) is preferably 1.1 to 1.7.

(D) Acid Diffusion Control Agent

The photoresist composition preferably contains (D) an acid diffusion control agent (except for those falling under the compound (B)). The acid diffusion control agent (D) exhibits the effects of controlling a diffusion phenomenon of an acid generated from the compound (B) upon an exposure in the resist film, and of inhibiting unfavorable chemical reactions in an unexposed region. When the photoresist composition further contains the acid diffusion control agent (D), a resist pattern that is more superior in pattern developability and LWR performance can be formed.

The acid diffusion control agent (D) is exemplified by an amine compound, an amide group-containing compound, a urea compound, a nitrogen-containing heterocyclic compound, and the like.

Examples of the amine compound include mono(cyclo) alkylamines; di(cyclo)alkylamines; tri(cyclo)alkylamines; substituted alkylanilines and derivatives thereof; ethylenediamine, N,N,N',N'-tetramethylethylenediamine, tetramethylenediamine, hexamethylenediamine, 4,4'-diaminodiphenylmethane, 4,4'-diaminodiphenyl ether, 4,4'-diaminobenzophenone, 4,4'-diaminodiphenylamine, 2,2-bis(4-aminophenyl)propane, 2-(3-aminophenyl)-2-(4-aminophenyl)propane, 2-(4-aminophenyl)-2-(3-hydroxyphenyl)propane, 2-(4-aminophenyl)-2-(4-hydroxyphenyl)propane, 1,4-bis(1-(4-aminophenyl)-1-methylethyl)benzene, 1,3-bis(1-(4-aminophenyl)-1-methylethyl)benzene, bis(2-dimethylaminoethyl)ether, bis(2-diethylaminoethyl)ether, 1-(2-hydroxyethyl)-2-imidazolidinone, 2-quinoxalinol, N,N,N',N'-tetrakis(2-hydroxypropyl)ethylenediamine, N,N,N',N"N"-pentamethyldiethylenetriamine, and the like.

Examples of the amide group-containing compound include N-t-butoxycarbonyl group-containing amino compounds such as N-t-butoxycarbonyl-di-n-octylamine, N-t-amyloxycarbonyl-di-n-octylamine, N-t-butoxycarbonyl-di-n-nonylamine, N-t-amyloxycarbonyl-di-n-nonylamine, N-t-butoxycarbonyl-di-n-decylamine, N-t-amyloxycarbonyl-di-n-decylamine, N-t-butoxycarbonyl-dicyclohexylamine, N-t-amyloxycarbonyl-dicyclohexylamine, N-t-butoxycarbonyl-1-adamantylamine, N-t-amyloxycarbonyl-1-adamantylamine, N-t-butoxycarbonyl-2-adamantylamine, N-t-amyloxycarbonyl-2-adamantylamine, N-t-butoxycarbonyl-N-methyl-1-adamantylamine, N-t-amyloxycarbonyl-N-methyl-1-adamantylamine, (S)-(−)-1-(t-butoxycarbonyl)-2-pyrrolidinemethanol, (S)-(−)-1-(t-amyloxycarbonyl)-2-pyrrolidinemethanol, (R)-(+)-1-(t-butoxycarbonyl)-2-pyrrolidinemethanol, (R)-(+)-1-(t-amyloxycarbonyl)-2-pyrrolidinemethanol, N-t-butoxycarbonyl-4-hydroxypiperidine, N-t-amyloxycarbonyl-4-hydroxypiperidine, N-t-butoxycarbonylpyrrolidine, N-t-amyloxycarbonylpyrrolidine, N,N'-di-t-butoxycarbonylpiperazine, N,N'-di-t-amyloxycarbonylpiperazine, N,N-di-t-butoxycarbonyl-1-adamantylamine, N,N-di-t-amyloxycarbonyl-1-adamantylamine, N-t-butoxycarbonyl-4,4'-diaminodiphenylmethane, N-t-amyloxycarbonyl-4,4'-diaminodiphenylmethane, N,N'-di-t-butoxycarbonylhexamethylenediamine, N,N'-di-t-amyloxycarbonylhexamethylenediamine, N,N,N',N'-tetra-t-butoxycarbonylhexamethylenediamine, N,N,N',N'-tetra-t-amyloxycarbonylhexamethylenediamine, N,N'-di-t-butoxycarbonyl-1,7-diaminoheptane, N,N'-di-t-amyloxycarbonyl-1,7-diaminoheptane, N,N'-di-t-butoxycarbonyl-1,8-diaminooctane, N,N'-di-t-amyloxycarbonyl-1,8-diaminooctane, N,N'-di-t-butoxycarbonyl-1,9-diaminononane, N,N'-di-t- amyloxycarbonyl-1,9-diaminononane, N,N'-di-t-butoxycarbonyl-1,10-diaminodecane, N,N'-di-t-amyloxycarbonyl-1,10-diaminodecane, N,N'-di-t-butoxycarbonyl-1,12-diaminododecane, N,N'-di-t-amyloxycarbonyl-1,12-diaminododecane, N,N'-di-t-butoxycarbonyl-4,4'-diaminodiphenylmethane, N,N'-di-t-amyloxycarbonyl-4,4'-diaminodiphenylmethane, N-t-butoxycarbonylbenzimidazole, N-t-amyloxycarbonyl-2-methylbenzimidazole, N-t-butoxycarbonyl-2-phenylbenzimidazole and N-t-amyloxycarbonyl-2-phenylbenzimidazole, and the like.

Examples of the urea compound include urea, methylurea, 1,1-dimethylurea, 1,3-dimethylurea, 1,1,3,3-tetramethylurea, 1,3-diphenylurea, tri-n-butylthiourea, and the like.

Examples of the nitrogen-containing heterocyclic compound include imidazoles such as 2-phenylimidazole; pyridines; piperazines; and the like.

Furthermore, an onium salt compound that is degraded upon an exposure to lose its basicity that is responsible for an acid diffusion controlling ability may be used as the acid diffusion control agent (D). Examples of the onium salt compound include a sulfonium salt compound represented by the following formula (7-1), an iodonium salt compound represented by the following formula (7-2), and the like.

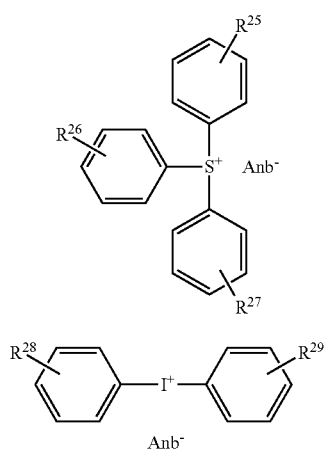

In the above formulae (7-1) and (7-2), $R^{25}$ to $R^{29}$ each independently represent a hydrogen atom, an alkyl group, an alkoxy group, a hydroxy group or a halogen atom; and Anb⁻ represents OH⁻, $R^{30}$—COO⁻, $R^{30}$—SO₃⁻, or an anion represented by the following formula (8), wherein $R^{30}$ represents an alkyl group, an aryl group or an alkanol group.

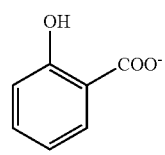

Examples of the sulfonium salt compound and the iodonium salt compound include triphenylsulfonium hydroxide, triphenylsulfonium acetate, triphenylsulfonium salicylate, diphenyl-4-hydroxyphenylsulfonium hydroxide, diphenyl-4-hydroxyphenylsulfonium acetate, diphenyl-4-hydroxyphenylsulfonium salicylate, bis(4-t-butylphenyl)iodonium hydroxide, bis(4-t-butylphenyl)iodonium acetate, bis(4-t-butylphenyl)iodonium hydroxide, bis(4-t-butylphenyl)iodonium acetate, bis(4-t-butylphenyl)iodonium salicylate, 4-t-butylphenyl-4-hydroxyphenyliodonium hydroxide, 4-t-butylphenyl-4-hydroxyphenyliodonium acetate, 4-t-butylphenyl-4-hydroxyphenyliodonium salicylate, bis(4-t-butylphenyl)iodonium 10-camphorsulfonate, diphenyliodonium 10-camphorsulfonate, triphenylsulfonium 10-camphorsulfonate, 4-t-butoxyphenyldiphenylsulfonium 10-camphorsulfonate, and the like.

Among these sulfonium salt compounds and iodonium salt compounds, triphenylsulfonium salicylate and triphenylsulfonium 10-camphorsulfonate are preferred.

The acid diffusion control agent (D) may be used in combination of two or more types thereof. The content of the acid diffusion control agent (D) with respect to 100 parts by mass of the polymer (A) is preferably no less than 0.1 parts by mass and no greater than 10 parts by mass, and more preferably no less than 0.1 parts by mass and no greater than 8 parts by mass. When the content of the acid diffusion control agent (D) falls within the abovementioned range, the pattern developability and the LWR performance may be further improved.

(E) Solvent

The photoresist composition typically contains the solvent (E). A solvent that can uniformly dissolve or disperse each component but does not react with each component is suitably used as the solvent (E). The solvent (E) is exemplified by an alcohol, an ether, a ketone, an amide, an ester, a hydrocarbon, and the like. It is to be noted that these solvents may be used in combination of two or more types thereof.

Examples of the alcohol include:

monohydric alcohols such as methanol, ethanol, n-propanol, iso-propanol, n-butanol, iso-butanol, sec-butanol, tert-butanol, n-pentanol, iso-pentanol, 2-methylbutanol, sec-pentanol, tert-pentanol, 3-methoxybutanol, n-hexanol, 2-methylpentanol, sec-hexanol, 2-ethylbutanol, sec-heptanol, 3-heptanol, n-octanol, 2-ethylhexanol, sec-octanol, n-nonyl alcohol, 2,6-dimethyl-4-heptanol, n-decanol, sec-undecyl alcohol, trimethylnonyl alcohol, sec-tetradecyl alcohol, sec-heptadecyl alcohol, furfuryl alcohol, phenol, cyclohexanol, methylcyclohexanol, 3,3,5-trimethylcyclohexanol, benzyl alcohol and diacetone alcohol;

polyhydric alcohols such as ethylene glycol, 1,2-propylene glycol, 1,3-butylene glycol, 2,4-pentanediol, 2-methyl-2,4-pentanediol, 2,5-hexanediol, 2,4-heptanediol, 2-ethyl-1,3-hexanediol, diethylene glycol, dipropylene glycol, triethylene glycol and tripropylene glycol;

polyhydric alcohol partial ethers such as ethylene glycol monomethyl ether, ethylene glycol monoethyl ether, ethylene glycol monopropyl ether, ethylene glycol monobutyl ether, ethylene glycol monohexyl ether, ethylene glycol monophenyl ether, ethylene glycol mono-2-ethylbutyl ether, diethylene glycol monomethyl ether, diethylene glycol monoethyl ether, diethylene glycol monopropyl ether, diethylene glycol monobutyl ether, diethylene glycol monohexyl ether, propylene glycol monomethyl ether, propylene glycol monoethyl ether, propylene glycol monopropyl ether, propylene glycol monobutyl ether, dipropylene glycol monomethyl ether, dipropylene glycol monoethyl ether and dipropylene glycol monopropyl ether; and the like.

Examples of the ether include diethyl ether, dipropyl ether, dibutyl ether, diphenyl ether, methoxybenzene, and the like.

Examples of the ketone include ketones such as acetone, methyl ethyl ketone, methyl n-propyl ketone, methyl n-butyl ketone, diethyl ketone, methyl iso-butyl ketone, methyl n-pentyl ketone, ethyl n-butyl ketone, methyl n-hexyl ketone, di-iso-butyl ketone, trimethylnonanone, cyclopentanone, cyclohexanone, cycloheptanone, cyclooctanone, methylcyclohexanone, 2,4-pentanedione, acetonylacetone and acetophenone.

Examples of the amide include N,N'-dimethylimidazolidinone, N-methylformamide, N,N-dimethylformamide, N,N-diethylformamide, acetamide, N-methylacetamide, N,N-dimethylacetamide, N-methylpropionamide, N-methylpyrrolidone, and the like.

Examples of the ester include diethyl carbonate, propylene carbonate, methyl acetate, ethyl acetate, γ-butyrolactone, γ-valerolactone, n-propyl acetate, iso-propyl acetate, n-butyl acetate, iso-butyl acetate, sec-butyl acetate, n-pentyl acetate, sec-pentyl acetate, 3-methoxybutyl acetate, methylpentyl acetate, 2-ethylbutyl acetate, 2-ethylhexyl acetate, benzyl acetate, cyclohexyl acetate, methylcyclohexyl acetate, n-nonyl acetate, methyl acetoacetate, ethyl acetoacetate, ethylene glycol monomethyl ether acetate, ethylene glycol monoethyl ether acetate, diethylene glycol monomethyl ether acetate, diethylene glycol monoethyl ether acetate, diethylene glycol mono-n-butyl ether acetate, propylene glycol monomethyl ether acetate, propylene glycol monoethyl ether acetate, propylene glycol monopropyl ether acetate, propylene glycol monobutyl ether acetate, dipropylene glycol monomethyl ether acetate, dipropylene glycol monoethyl ether acetate, glycol diacetate, methoxytriglycol acetate, ethyl propionate, n-butyl propionate, iso-amyl propionate, diethyl oxalate, di-n-butyl oxalate, methyl lactate, ethyl lactate, n-butyl lactate, n-amyl lactate, diethyl malonate, dimethyl phthalate, diethyl phthalate, γ-butyrolactone, and the like.

Examples of the hydrocarbon include:

aliphatic hydrocarbons such as n-pentane, iso-pentane, n-hexane, iso-hexane, n-heptane, iso-heptane, 2,2,4-trimethylpentane, n-octane, iso-octane, cyclohexane and methylcyclohexane;

aromatic hydrocarbons such as benzene, toluene, xylene, mesitylene, ethylbenzene, trimethylbenzene, methylethylbenzene, n-propylbenzene, iso-propylbenzene, diethylbenzene, iso-butylbenzene, triethylbenzene, di-iso-propylbenzene and n-amylnaphthalene; and the like.

Among these, propylene glycol monomethyl ether acetate, cyclohexanone, γ-butyrolactone and ethyl lactate are preferred.

Other Optional Component

The photoresist composition may contain other optional component such as a surfactant and a sensitizing agent, within a range not leading to impairment of the effects of the present invention. It is to be noted that the photoresist composition may contain two or more types of the aforementioned other optional components.

Surfactant

The surfactant exerts the effect of improving a coating property, striation, developability and the like. Examples of the surfactant include nonionic surfactants such as polyoxyethylene lauryl ether, polyoxyethylene stearyl ether, polyoxyethylene oleyl ether, polyoxyethylene n-octylphenyl ether, polyoxyethylene n-nonylphenyl ether, polyethylene glycol dilaurate and polyethylene glycol distearate. Commercially available products include, for example, KP341 (manufactured by Shin-Etsu Chemical Co., Ltd.); Polyflow No. 75 and No. 95 (each manufactured by Kyoeisha Chemical Co., Ltd.); EFTOP EF301, EF303 and EF352 (each manufactured by Tochem Products Co. Ltd.); Megaface F171 and F173 (each manufactured by Dainippon Ink And Chemicals, Incorporated); Fluorad FC430 and FC431 (each manufactured by Sumitomo 3M Limited); ASAHI GUARD AG710, Surflon S-382, SC-101, SC-102, SC-103, SC-104, SC-105 and SC-106 (each manufactured by Asahi Glass Co., Ltd.); and the like.

Sensitizing Agent

The sensitizing agent exhibits the action of increasing the amount of an acid generated from the acid generating agent, which is the compound (B), and exerts the effect of improving "apparent sensitivity" of the photoresist composition. Examples of the sensitizing agent include carbazoles, acetophenones, benzophenones, naphthalenes, phenols, biacetyl, eosin, rose bengal, pyrenes, anthracenes, phenothiazines, and the like.

Preparation Method of Photoresist Composition

The photoresist composition may be prepared, for example, by mixing the polymer (A), the compound (B), the fluorine atom-containing polymer (C) and the acid diffusion control agent (D) as well as other optional component as needed in a predetermined ratio in the solvent (E). In addition, the resulting liquid mixture is preferably filtered through a filter with a pore size of about 0.20 μm. The solid content concentration of the photoresist composition is preferably no less than 0.1% by mass and no greater than 50% by mass, and more preferably no less than 0.5% by mass and no greater than 30% by mass.

Resist Pattern-Forming Method

A method for forming a resist pattern according to another embodiment of the present invention includes:

providing a resist film on a substrate using the photoresist composition (hereinafter, may be also referred to as "resist film-providing step"), exposing the resist film through a photomask (hereinafter, may be also referred to as "exposure step"), and developing the resist film exposed (hereinafter, may be also referred to as "development step"). Hereinafter, each step will be explained.

Resist Film-Providing Step

In this step, the photoresist composition is coated on a substrate by an appropriate coating means such as spin-coating, cast coating and roll coating to provide a resist film. Examples of the substrate include silicon wafers, silicon dioxide, wafers coated with antireflective film, and the like. Specifically, after the photoresist composition is coated such that the resulting resist film has a predetermined film thickness, prebaking (PB) is carried out to permit the solvent in the coating film to be volatilized, resulting in the formation of the resist film. The temperature of PB is typically 60° C. to 140° C., and preferably 80° C. to 120° C. The time period of PB is typically 5 sec to 600 sec, and preferably 10 sec to 300 sec.

Exposure Step

In this step, the resist film provided in the resist film-providing step is exposed at a desired region through a mask. Moreover, in this step, the exposure may be conducted by carrying out reduced projection through a liquid immersion liquid as needed. For example, an isolated trench (iso-trench) pattern can be formed by carrying out reduced projection exposure at a desired region through a mask having an isolated line (iso-line) pattern. Also, the exposure may be carried out at least twice. When the exposure is carried out at least twice, the exposure is preferably carried out continuously. When the exposure is carried out a plurality of times, for example, a first reduced projection exposure is carried out through a line-and-space pattern mask at a desired region, and subsequently a second reduced projection exposure is carried out such that lines cross over the light-exposed site subjected to the first exposure. The first light-exposed site is preferably orthogonal to the second light-exposed site. Due to being orthogonal with each other, a circular contact hole pattern can be easily formed at light-unexposed site surrounded by the light-exposed site.

Examples of the liquid immersion liquid which may be used in the exposure include water, fluorine-containing inert liquids, and the like. It is preferred that the liquid immersion liquid is transparent to the exposure wavelength, and has a temperature coefficient of the refractive index as small as possible so that distortion of an optical image projected onto the film is minimized. When an ArF excimer laser beam (wavelength: 193 nm) is used as the exposure light source, water is preferably used as the liquid immersion liquid in light of its availability and ease of handling, in addition to the aforementioned respects. When water is used, a marginal amount of an additive which reduces the surface tension of water and imparts enhanced surfactant power may be added. It is preferred that the additive hardly dissolves a resist layer on a wafer and has a negligible influence on an optical coating of an inferior face of a lens. The water for use is preferably distilled water.

A radioactive ray which may be used in the exposure is appropriately selected in accordance with the type of the acid generating agent which is the compound (B), and examples thereof include ultraviolet rays, far ultraviolet rays, X-rays, electron beams, and the like. Among these, far ultraviolet rays typified by an ArF excimer laser beam or a KrF excimer laser beam (wavelength: 248 nm) and electron beams are preferred, and an ArF excimer laser beam and electron beams are more preferred. The exposure conditions such as an exposure dose may be appropriately selected in accordance with the formulation of the photoresist composition, the type of the additive, and the like. The resist pattern-forming method according to the embodiment of the present invention may include a plurality of exposure steps, and the light sources employed in the plurality of exposure steps may be identical or different, but an ArF excimer laser beam is preferably used in the first exposure.

It is preferred that post exposure baking (PEB) is carried out after the exposure. Carrying out the PEB serves in smoothly proceeding a dissociation reaction of an acid-labile group in the photoresist composition. The baking conditions of the PEB involves typically no less than 30° C. and less than 200° C., and preferably no less than 50° C. and less than 150° C. At the temperature of less than 30° C., the dissociation reaction may not smoothly proceed, whereas at the temperature of no less than 200° C., an acid generated from the acid generating agent which is the compound (B) may widely diffuse to light-unexposed sites, and as a result, a favorable pattern may not be obtained. The time period of the PEB is typically 5 sec to 600 sec, and preferably 10 sec to 300 sec.

Development Step

In this step, the resist film exposed is developed with a developer solution. After the development, washing with water followed by drying is typically carried out. As the developer solution, an aqueous alkali solution prepared by dissolving at least one of alkaline compounds such as e.g., sodium hydroxide, potassium hydroxide, sodium carbonate, sodium silicate, sodium metasilicate, aqueous ammonia, ethylamine, n-propylamine, diethylamine, di-n-propylamine, triethylamine, methyldiethylamine, ethyldimethylamine, triethanolamine, tetramethylammonium hydroxide (TMAH), pyrrole, piperidine, choline, 1,8-diazabicyclo-[5.4.0]-7-undecene and 1,5-diazabicyclo-[4.3.0]-5-nonene is preferred.

Examples of the development method include: a method (dip coating method) including immersing the substrate for a given time period in a container filled with the developer solution; a method (puddle method) including placing the developer solution to form a dome-shaped bead by way of the surface tension on the surface of the substrate for a given time period to conduct a development; a method (spray coating method) including spraying the developer solution onto the surface of the substrate; a method (dynamic dispensing method) including continuously applying the developer solution onto the substrate that is rotated at a constant speed while scanning with a developer solution application nozzle at a constant speed; and the like.

Compound (1)

The compound (1) according to still another embodiment of the present invention is the compound (B). The compound (1) is represented by the aforementioned formula (1). When the compound (1) has the specific structure, a photoresist composition containing the compound (1) exhibits superior resolving ability and a superior LWR performance.

Acid Generating Agent

The acid generating agent according to yet still another embodiment of the present invention contains the compound (1), wherein n is an integer of 1 to 5; and $R^3$ and $R^4$ that bond to the carbon atom adjacent to the $SO_3^-$ group among $R^3(s)$ and $R^4(s)$ in the above formula (1) represent a fluorine atom or a perfluoroalkyl group. When the acid generating agent contains the compound having the specific structure, the acid generating agent includes a hydroxy group after the exposure while the acidity of the generated acid can be properly enhanced. As a result, the resolving ability and LWR performance of the photoresist composition that contains the acid generating agent can be improved.

Photodegradable Base

The photodegradable base according to even yet still another embodiment of the present invention contains the compound (1), wherein n is an integer of 1 to 5; and $R^3$ and $R^4$ that bond to the carbon atom adjacent to the $SO_3^-$ group among $R^3(s)$ and $R^4(s)$ in the above formula (1) represent a hydrogen atom or an alkyl group having 1 to 10 carbon atoms. When the photodegradable base according to the even yet still another embodiment of the present invention contains the compound having the specific structure, a diffusing acid can be trapped at a light-unexposed site, whereas the function of trapping the acid is lost at a light-exposed site. As a result, the resolving ability and LWR performance of the photoresist composition that contains the photodegradable base can be improved.

EXAMPLES

Hereinafter, the present invention will be described in detail by way of Examples, but the present invention shall not be construed as being limited thereto. Measuring methods for various types of physical properties are shown below.

Weight Average Molecular Weight (Mw), Number Average Molecular Weight (Mn) and Dispersity Index (Mw/Mn)

The Mw and Mn of the polymer were determined by gel permeation chromatography (GPC) using GPC columns (G2000HXL×2, G3000HXL×1 and G4000HXL×1) manufactured by Tosoh Corporation under the following conditions. In addition, the dispersity index (Mw/Mn) was calculated based on the results of the determination of the Mw and Mn.

elution solvent: tetrahydrofuran
flow rate: 1.0 mL/min
sample concentration: 1.0% by mass
amount of injected sample: 100 μL
column temperature: 40° C.
detector: differential refractometer
standard substance: mono-dispersed polystyrene Content of Low Molecular Weight Component The content (% by mass) of a low molecular weight component in the polymer (A) was determined on a high performance liquid chromatography (HPLC) using an Intersil ODS-25 μm column (4.6 mm)×250 mm) manufactured by GL Sciences, Inc., under the following conditions. It is to be noted that the low molecular weight component means a component that contains a monomer as a principal component and has a molecular weight of less than 1,000.

elution solvent: acrylonitrile/0.1% by mass aqueous phosphoric acid solution
flow rate: 1.0 mL/min
sample concentration: 1.0% by mass
amount of injected sample: 100 μL
detector: differential refractometer $^{13}$C-NMR Analysis $^{13}$C-NMR analysis was conducted using JNM-EX270 (manufactured by JEOL, Ltd.), and DMSO-$d_6$ was used as a solvent for a measurement. The proportion of each structural unit in a polymer was calculated from an area ratio of peaks corresponding to the respective structural units in a spectrum obtained by $^{13}$C-NMR.

Synthesis of Compound (i)

Example 1

The compound (1) (acid generating agent (B-1)) was synthesized in accordance with the following scheme.

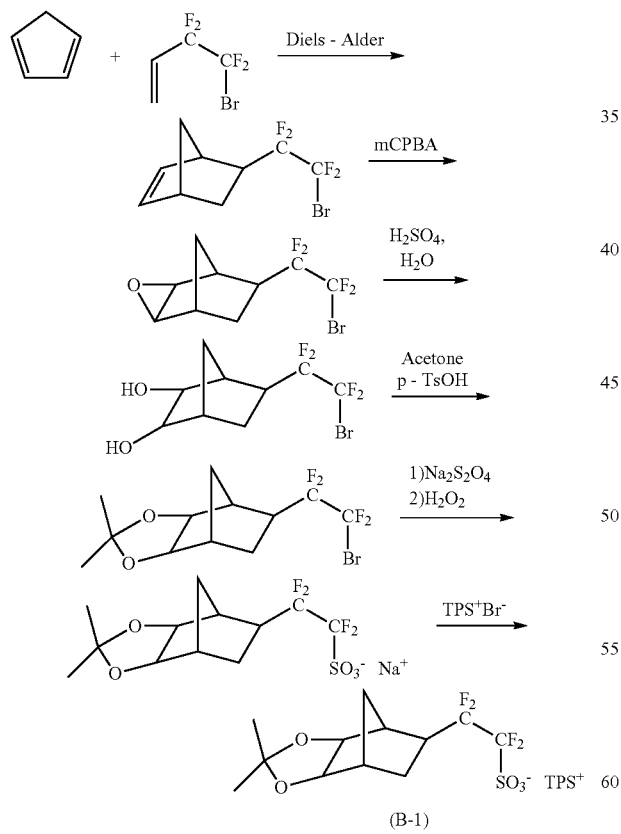

(B-1)

4-Bromo-3,3,4,4-tetrafluoro-1-butene and one equivalent of dicyclopentadiene were mixed, and the mixture was heated at 170° C. for 10 hours. A norbornene derivative was obtained after purification by column chromatography. The norbornene derivative was dissolved in dichloromethane to provide a 1 M solution, and 1.2 equivalents of m-chloroperoxybenzoic acid (mCPBA) was added to this solution with cooling at 0° C., followed by stirring at room temperature for 10 hours. The generated carboxylic acid was removed by filtration and washed twice with dichloromethane, and the solvent was distilled to obtain a crude epoxide derivative. To this, a liquid mixture of acetone:water:10% by mass sulfuric acid (5:2:3 (mass ratio)) was added to provide a 0.5 M solution, and the solution was stirred at 60° C. for 10 hours. After extraction with ethyl acetate, the extract was washed with an aqueous sodium thiosulfate solution and then with an aqueous sodium bicarbonate solution to obtain a diol derivative. The diol derivative was dissolved in 30 equivalents of acetone, to this was added 0.1 equivalents of p-TsOH, and the mixture was refluxed for 10 hours. Purification by column chromatography gave an acetal-protected form. After a liquid mixture of acetonitrile:water (1:1 (mass ratio)) was added to the acetal-protected form to provide a 1 M solution, 1.5 equivalents of sodium dithionite and 1.7 equivalents of sodium bicarbonate were added to the solution, and the reaction was allowed to proceed at 60° C. for 8 hours. After extraction with acetonitrile followed by distillation of the solvent, a liquid mixture of acetonitrile:water (3:1 (mass ratio)) was added to provide a 0.5 M solution. To this solution were added 1.25 equivalents of aqueous hydrogen peroxide and 0.05 equivalents of sodium tungstate, and the mixture was allowed to stir at 50° C. for 5 hours. Extraction with acetonitrile followed by distillation of the solvent gave a sulfonic acid compound. To this compound was added one equivalent of triphenylsulfonium chloride, and a liquid mixture of water and dichloromethane (mass ratio of water:dichloromethane=1:3) was added to provide a 0.5 M solution. After vigorous stirring at room temperature for 6 hours followed by extraction with dichloromethane and washing with water, (B-1) was obtained.

Synthesis of Polymer

The monomers used in the synthesis of the polymer (A) and the fluorine atom-containing polymer (C) as described later are shown below.

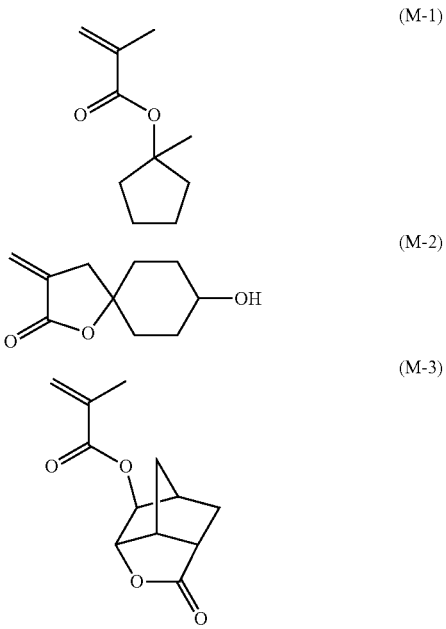

-continued

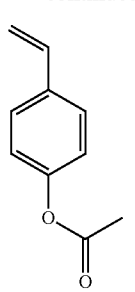
(M-4)

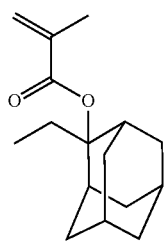
(M-5)

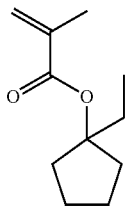
(M-6)

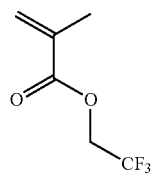
(M-7)

It is to be noted that: the compounds (M-1), (M-5) and (M-6) give the structural unit (I); the compound (M-3) gives the structural unit (II); the compounds (M-2) and (M-4) give the structural unit (III); and the compound (M-7) gives the structural unit (IV).

Synthesis of Polymer (A)

Synthesis Example 1

A monomer solution was prepared by dissolving 27.16 g (60 mol %) of the compound (M-1), 4.90 g (10 mol %) of the compound (M-2), and 17.94 g (30 mol %) of the compound (M-3) in 50 g of 2-butanone, and adding thereto 2.21 g (5 mol % with respect to the total number of moles of the monomers) of azobisisobutyronitrile (AIBN) as a radical initiator. Subsequently, 50 g of 2-butanone was charged into a 300 mL three-neck flask, and then the three-neck flask was purged with a nitrogen gas for 30 min. Thereafter the contents of the three-neck flask were heated to 80° C. while stirring with a magnetic stirrer, and the monomer solution prepared above was added dropwise over 3 hours with a dropping funnel. The time of the start of the dropwise addition was regarded as the time of the start of the polymerization reaction, and the polymerization reaction was allowed to proceed for 6 hours. After completing the polymerization, the polymerization solution was water-cooled to 30° C. or below. The cooled polymerization solution was poured into 750 g of methanol, and a deposited white powder was filtered off. The filtered white powder was washed twice with 150 g of methanol, then filtered, and thereafter dried at 50° C. for 17 hours to obtain a polymer (A-1) as a white powder (38.6 g; yield: 77%). The polymer (A-1) had an Mw of 7,600 and an Mw/Mn of 1.63. The result of $^{13}$C-NMR analysis indicated that the proportions of structural units derived from the compounds (M-1), (M-2) and (M-3) were 60.2 mol %, 9.6 mol % and 30.2 mol %, respectively. In addition, the content of the low molecular weight component in the polymer (A-1) was 0.04% by mass.

Synthesis Example 2

After 55.0 g (65 mol %) of the compound (M-4) and 45.0 g (35 mol %) of the compound (M-5), 4 g (5 mol % with respect to the total number of moles of the monomers) of AIBN as well as 1 g of t-dodecyl mercaptan were dissolved in 100 g of propylene glycol monomethyl ether, the polymerization was allowed to proceed for 16 hours under a nitrogen atmosphere, while maintaining the reaction temperature of 70° C. After the polymerization, the reaction solution was added dropwise into 1,000 g of n-hexane, and a copolymer was solidified and purified. Then, after 150 g of propylene glycol monomethyl ether was again added to the copolymer, 150 g of methanol, 34 g of triethylamine and 6 g of water were further added, and the hydrolysis reaction was allowed to proceed for 8 hours while the mixture was refluxed at the boiling point thereof. After the reaction, the solvent and triethylamine were distilled under vacuum. The obtained copolymer was dissolved in 150 g of acetone, and then added dropwise into 2,000 g of water to permit solidification. The formed white powder was filtered, dried at 50° C. for 17 hours to obtain a polymer (A-2) as a white powder (65.7 g; yield: 76.6%). The polymer (A-2) had an Mw of 10,000 and an Mw/Mn of 2.1. The result of $^{13}$C-NMR analysis indicated that the proportions of the structural unit derived from p-hydroxystyrene and the structural unit derived from the compound (M-5) were 65.4 mol % and 34.6 mol %, respectively. In addition, the content of the low molecular weight component in the polymer (A-2) was 0.05% by mass.

Synthesis of Fluorine Atom-Containing Polymer (C)

Synthesis Example 3

A monomer solution was prepared by dissolving 79.9 g (70 mol %) of the compound (M-6) and 20.91 g (30 mol %) of the compound (M-7) in 100 g of 2-butanone, and adding thereto 4.77 g of dimethyl 2,2'-azobisisobutyrate. A 1,000 mL three-neck flask containing 100 g of 2-butanone was purged with a nitrogen gas for 30 min, and then the monomer solution prepared above was added dropwise over 3 hours with a dropping funnel with heating at 80° C. and stirring. The time of the start of the dropwise addition was regarded as the time of the start of the polymerization reaction, and the polymerization reaction was allowed to proceed for 6 hours. After completing the polymerization, the polymerization solution was water-cooled to 30° C. or below. After the reaction solution was transferred to a 2 L separatory funnel, the polymerization solution was homogeneously diluted with 150 g of n-hexane and 600 g of methanol was charged, followed by mixing. Then, 30 g of distilled water was charged, followed by further stirring, and the mixture was left to stand for 30 min. Thereafter, the lower layer was recovered to give a propylene glycol monomethyl ether acetate solution (yield: 60%). The obtained polymer (C-1) had an Mw of 7,200 and an Mw/Mn of 2.00, and the content of the low molecular weight component was 0.07% by mass. In addition, the result of $^{13}$C-NMR analysis indicated that the proportions of structural units derived from (M-6) and (M-7) were 71.1 mol % and 28.9 mol %, respectively.

Preparation of Photoresist Composition

Components other than the polymer (A), the compound (B) (compound (1)) and the fluorine atom-containing polymer (C), used in the preparation of each photoresist composition are shown below.

(D) Acid Diffusion Control Agent compound represented by the following formula (D-1): N-t-butoxycarbonyl-4-hydroxypiperidine

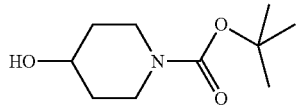

(D-1)

(E) Solvent

E-1: propylene glycol monomethyl ether acetate
E-2: ethyl lactate

Example 2

One hundred parts by mass of (A-1) as the polymer (A), 7.87 parts by mass of the acid generating agent (B-1) as the compound (B), 3 parts by mass of (C-1) as the fluorine atom-containing polymer (C), 0.945 parts by mass of (D-1) as the acid diffusion control agent (D), and 3,500 parts by mass of (E-1) as the solvent (E) were mixed, and the obtained mixed solution was filtered through a filter with a pore size of 0.20 μm to prepare a photoresist composition (J-1).

Example 3

One hundred parts by mass of (A-2) as the polymer (A), 15.7 parts by mass of the acid generating agent (B-1) as the compound (B), 1.89 parts by mass of (D-1) as the acid diffusion control agent (D), 3,300 parts by mass of (E-1) and 1,400 parts by mass of (E-2) as the solvent (E) were mixed, and the obtained mixed solution was filtered through a filter with a pore size of 0.20 μm to prepare a photoresist composition (J-2).

Formation of Resist Pattern

Example 4

Use of ArF Excimer Laser Beam in Exposure

An underlayer antireflective film having a film thickness of 105 nm was provided on a 12-inch silicon wafer by coating a composition for forming an underlayer antireflective film (ARC66, manufactured by Brewer Science) on the 12-inch silicon wafer with a spin coater (CLEAN TRACK ACT12, manufactured by Tokyo Electron Limited), and thereafter subjecting the same to heating at 205° C. for 60 sec. Then, the photoresist composition (J-1) was coated using the spin coater, and thereafter subjected to PB at 100° C. for 60 sec. Subsequently, cooling was carried out at 23° C. for 30 sec to provide a resist film having a film thickness of 90 nm. Next, an exposure was carried out through a mask pattern under the best focus conditions using an ArF Immersion Scanner (NSR-S610C, manufactured by Nikon Precision Inc.) under optical conditions involving NA of 1.3 and dipole (Sigma being 0.977/0.782). Subsequently, PEB was carried out at 120° C. for 60 sec. A development was carried out at 23° C. for 60 sec using a 2.38% by mass aqueous tetramethylammonium hydroxide solution, followed by rinsing with pure water and drying to form a resist pattern.

Example 5

Use of Electron Beam in Exposure

The photoresist composition (J-2) was coated on an 8-inch silicon wafer with a spin coater (CLEAN TRACK ACT12, manufactured by Tokyo Electron Limited), and was subjected to PB at 110° C. for 60 sec. Subsequently, cooling was carried out at 23° C. for 30 sec to provide a resist film having a film thickness of 50 nm. Subsequently, the resist film was irradiated with an electron beam using a simplified electron beam writer (manufactured by Hitachi, Ltd., model "HL800D", power: 50 KeV; electric current density: 5.0 ampere/cm$^2$). Subsequently, PEB was carried out at 90° C. for 60 sec. A development was carried out at 23° C. for 60 sec using a 2.38% aqueous tetramethylammonium hydroxide solution, followed by rinsing with pure water and drying to form a resist pattern.

Evaluations

Using each photoresist composition prepared above, a resist pattern was formed according to the above-described method, and the following evaluations were made. The results are shown in Table 1. It is to be noted that a scanning electron microscope (CG4000, manufactured by Hitachi High-Technologies Corporation) was used for the measurement in each evaluation.

Sensitivity

For the photoresist composition (J-1), when a positive resist pattern was formed, an exposure dose at which a line-and-space pattern of 1:1 (1 L1 S) having a line width of 40 nm was formed was designated as optimum exposure dose, and the optimum exposure dose was regarded as sensitivity (mJ/cm$^2$). On the other hand, for the photoresist composition (J-2), an exposure dose at which a line-and-space pattern of 1:1 (1L1S) having a line width of 40 nm was formed was designated as optimum exposure dose, and the optimum exposure dose was regarded as sensitivity (μC/cm$^2$). The sensitivity of no greater than 50 (mJ/cm$^2$) or no greater than 60 (μC/cm$^2$) may be evaluated to be favorable.

Resolution (nm)

A dimension of the minimum resist pattern which was obtained when a pattern formed in the pattern-forming method was resolved at the optimum exposure dose was designated as resolution (nm). In a case where an ArF excimer laser beam was used in the exposure, a resolution of no greater than 40 (nm) was evaluated to be favorable. On the other hand, in a case where an electron beam was used, a resolution of no greater than 70 (nm) was evaluated to be favorable.

LWR Performance (nm)

The line-and-space pattern resolved at the optimum exposure dose was observed from above the pattern using a scanning electron microscope (CG-4000, manufactured by Hitachi High-Technologies Corporation). Then, the line width was measured at arbitrary points of 50 in total, and a 3 Sigma value was determined from the distribution of the measurements, and the value was regarded as an LWR (nm). In a case where an ArF excimer laser beam was used in the exposure, when a value of the LWR was no greater than 4.0 (nm), the shape of the resist pattern formed was evaluated to be favorable. On the other hand, in a case where an electron beam was used in the exposure, when a value of the LWR was no greater than 10.0 (nm), the shape of the resist pattern formed was evaluated to be favorable. It is to be noted that the scanning electron microscope (CG4000, manufactured by Hitachi High-Technologies Corporation) was also used for the measurement of the line width.

TABLE 1

| | Photoresist composition | Sensitivity | Resolution (nm) | LWR performance (nm) |
|---|---|---|---|---|
| Example 2 | J-1 | 38 (mJ/cm$^2$) | 32 | 2.8 |
| Example 3 | J-2 | 42 (μC/cm$^2$) | 60 | 8.7 |

As is clear from the results shown in Table 1, it was revealed that the photoresist composition according to the embodiment of the present invention enabled the resist pattern formed to exhibit superior resolving ability and a superior LWR performance in both the exposure using an ArF excimer laser beam and the exposure using an electron beam.

INDUSTRIAL APPLICABILITY

The photoresist composition, the resist pattern-forming method, the compound, the acid generating agent and the photodegradable base according to the embodiments of the present invention enable a resist pattern exhibiting a superior resolution and a decreased LWR to be formed. Therefore, the photoresist composition, the compound, the acid generating agent and the photodegradable base can be suitably used in lithography processes for which further miniaturization is desired.

The invention claimed is:

1. A photoresist composition, comprising:
a polymer comprising a structural unit that comprises an acid-labile group; and
a compound represented by formula (1-I):

$$\text{(1-I)}$$

wherein, in the formula (1-I),
$R^2$ represents a trivalent alicyclic hydrocarbon group having 3 to 20 carbon atoms;
$R^3$ and $R^4$ each independently represent a hydrogen atom, a fluorine atom, a monovalent hydrocarbon group having 1 to 20 carbon atoms or a monovalent fluorinated hydrocarbon group having 1 to 20 carbon atoms;
R' and R" each independently represent a hydrocarbon group having 1 to 10 carbon atoms, wherein R' and R" optionally taken together represent a ring structure by binding with each other, together with the carbon atom to which R' and R" bond;
n is an integer of 0 to 5, wherein in a case where $R^3$ and $R^4$ are each present in a plurality of number, a plurality of $R^3$s are identical to or different from each other, and a plurality of $R^4$s are identical to or different from each other; and
$M^+$ represents a monovalent radiation-degradable onium cation.

2. The photoresist composition according to claim 1, wherein the compound represented by the formula (1-I) is represented by formula (1-i):

$$\text{(1-i)}$$

wherein, in the formula (1-i),
n is an integer of 0 to 5;
R' and R" each independently represent a hydrocarbon group having 1 to 10 carbon atoms, wherein R' and R" optionally taken together represent a ring structure by binding with each other, together with the carbon atom to which R' and R" bond;
$R^{3\prime}$ and $R^{4\prime}$ each independently represent a fluorine atom or a perfluoroalkyl group, wherein in a case where $R^{3\prime}$ and $R^{4\prime}$ are each present in a plurality of number, a plurality of $R^{3\prime}$s are identical to or different from each other, and a plurality of $R^{4\prime}$s are identical to or different from each other; and
$M^+$ represents a monovalent radiation-degradable onium cation.

3. The photoresist composition according to claim 1, wherein n is an integer of 1 to 5; and among $R^3$(s) and $R^4$(s) in the formula (1-I), $R^3$ and $R^4$ that bond to the carbon atom adjacent to the $SO_3^-$ group represent a hydrogen atom or an alkyl group having 1 to 10 carbon atoms.

4. The photoresist composition according to claim 1, wherein the polymer comprising a structural unit that comprises an acid-labile group further comprises a structural unit that comprises a hydroxy group.

5. The photoresist composition according to claim 1, wherein $M^+$ in the formula (1-I) is represented by formula (2):

$$\text{(2)}$$

wherein, in the formula (2),
$R^5$ represents a fluorine atom, a hydroxy group, an alkyl group having 1 to 10 carbon atoms, an alkoxy group having 1 to 10 carbon atoms, an alkoxycarbonyl group having 2 to 11 carbon atoms, or an alkylsulfonyl group having 1 to 10 carbon atoms;
j is an integer of 0 to 9, wherein in a case where j is no less than 2, a plurality of $R^5$s are identical or different;
$R^6$ and $R^7$ each independently represent an alkyl group having 1 to 10 carbon atoms or an aryl group having 6 to 20 carbon atoms, wherein a part or all of hydrogen atoms included in the alkyl group and the aryl group are unsubstituted or substituted, and wherein $R^6$ and $R^7$ optionally taken together represent a ring structure having 2 to 10 carbon atoms by binding with each other, together with the sulfur atom to which $R^6$ and $R^7$ bond; and
k is an integer of 0 to 2.

6. The photoresist composition according to claim 1, wherein $R^2$ in the formula (1-I) represents a polycyclic alicyclic hydrocarbon group.

7. The photoresist composition according to claim 1, wherein n is an integer of 1 to 5; and among $R^3$(s) and $R^4$(s)

in the formula (1-I), $R^3$ and $R^4$ that bond to the carbon atom adjacent to the $SO_3^-$ group represent a fluorine atom or a perfluoroalkyl group.

8. The photoresist composition according to claim 1, wherein the compound comprises a first compound which functions as an acid generator and a second compound which functions as a photodegradable base.

9. The photoresist composition according to claim 1, wherein a content of the compound which functions as an acid generator is no less than 0.1 parts by mass and no greater than 20 parts by mass with respect to 100 parts by mass of the polymer.

10. The photoresist composition according to claim 1, wherein a content of the compound which functions as a photodegradable base is no less than 0.1 parts by mass and no greater than 15 parts by mass with respect to 100 parts by mass of the polymer.

11. The photoresist composition according to claim 1, further comprising a fluorine atom-containing polymer which comprises a fluorine atom and which has a content of the fluorine atom higher than a content of a fluorine atom of the polymer comprising a structural unit that comprises an acid-labile group.

12. A resist pattern-forming method, comprising:
applying the photoresist composition according to claim 1 on a substrate to provide a resist film;
exposing the resist film; and
developing the resist film exposed.

13. A compound represented by formula (1-I):

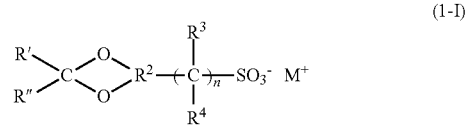

(1-I)

wherein, in the formula (1-I),
$R^2$ represents a trivalent alicyclic hydrocarbon group having 3 to 20 carbon atoms;
$R^3$ and $R^4$ each independently represent a hydrogen atom, a fluorine atom, a monovalent hydrocarbon group having 1 to 20 carbon atoms or a monovalent fluorinated hydrocarbon group having 1 to 20 carbon atoms;
R' and R" each independently represent a hydrocarbon group having 1 to 10 carbon atoms, wherein R' and R" optionally taken together represent a ring structure by binding with each other, together with the carbon atom to which R' and R" bond;
n is an integer of 0 to 5, wherein in a case where $R^3$ and $R^4$ are each present in a plurality of number, a plurality of $R^3$s are identical to or different from each other, and a plurality of $R^4$s are identical to or different from each other; and
$M^+$ represents a monovalent radiation-degradable onium cation.

14. A compound represented by formula (1-i):

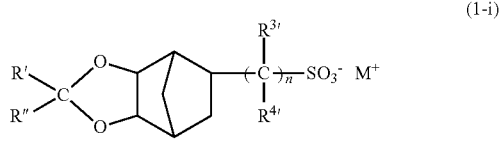

(1-i)

wherein, in the formula (1-i),
n is an integer of 0 to 5;
R' and R" each independently represent a hydrocarbon group having 1 to 10 carbon atoms, wherein R' and R" optionally taken together represent a ring structure by binding with each other, together with the carbon atom to which R' and R" bond;
$R^{3'}$ and $R^{4'}$ each independently represent a fluorine atom or a perfluoroalkyl group, wherein in a case where $R^{3'}$ and $R^{4'}$ are each present in a plurality of number, a plurality of $R^{3'}$s are identical to or different from each other, and a plurality of $R^{4'}$s are identical to or different from each other; and
$M^+$ represents a monovalent radiation-degradable onium cation.

15. An acid generating agent comprising the compound according to claim 13,
wherein n is an integer of 1 to 5; and among $R^3$(s) and $R^4$(s) in the formula (1-I), $R^3$ and $R^4$ that bond to the carbon atom adjacent to the $SO_3^-$ group represent a fluorine atom or a perfluoroalkyl group.

16. A photodegradable base comprising the compound according to claim 13,
wherein n is an integer of 1 to 5; and among $R^3$(s) and $R^4$(s) in the formula (1-I), $R^3$ and $R^4$ that bond to the carbon atom adjacent to the $SO_3^-$ group represent a hydrogen atom or an alkyl group having 1 to 10 carbon atoms.

17. The compound according to claim 13, wherein $M^+$ in the formula (1) is represented by formula (2):

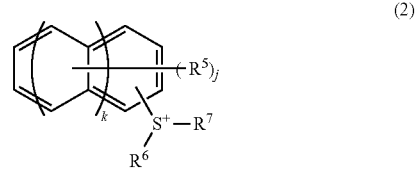

(2)

wherein, in the formula (2),
$R^5$ represents a fluorine atom, a hydroxy group, an alkyl group having 1 to 10 carbon atoms, an alkoxy group having 1 to 10 carbon atoms, an alkoxycarbonyl group having 2 to 11 carbon atoms, or an alkylsulfonyl group having 1 to 10 carbon atoms;
j is an integer of 0 to 9, wherein in a case where j is no less than 2, a plurality of $R^5$s are identical or different;
$R^6$ and $R^7$ each independently represent an alkyl group having 1 to 10 carbon atoms or an aryl group having 6 to 20 carbon atoms, wherein a part or all of hydrogen atoms included in the alkyl group and the aryl group are unsubstituted or substituted, and wherein $R^6$ and $R^7$ optionally taken together represent a ring structure having 2 to 10 carbon atoms by binding with each other, together with the sulfur atom to which $R^6$ and $R^7$ bond; and
k is an integer of 0 to 2.

18. The compound according to claim 13, wherein $R^2$ in the formula (1-I) represents a polycyclic alicyclic hydrocarbon group.

* * * * *